United States Patent
Kawai et al.

(10) Patent No.: US 9,545,415 B2
(45) Date of Patent: Jan. 17, 2017

(54) ANTI-INFLAMMATORY COMPOUNDS IN COMBINATION WITH HYDROGEN FOR THE TREATMENT OF INFLAMMATION

(71) Applicant: SKYVIEW ENTERPRISE LTD., New York, NY (US)

(72) Inventors: Toshihisa Kawai, Brookline, MA (US); Kenneth I. Kohn, West Bloomfield, MI (US)

(*) Notice: Subject to any disclaimer, the term of this patent is extended or adjusted under 35 U.S.C. 154(b) by 56 days.

(21) Appl. No.: 14/370,842

(22) PCT Filed: Jan. 4, 2013

(86) PCT No.: PCT/US2013/020298
§ 371 (c)(1),
(2) Date: Jul. 7, 2014

(87) PCT Pub. No.: WO2013/103826
PCT Pub. Date: Jul. 11, 2013

(65) Prior Publication Data
US 2015/0140090 A1 May 21, 2015

Related U.S. Application Data

(60) Provisional application No. 61/583,903, filed on Jan. 6, 2012, provisional application No. 61/595,304, filed
(Continued)

(51) Int. Cl.
| | |
|---|---|
| *A61K 9/48* | (2006.01) |
| *A61K 31/7016* | (2006.01) |
| *A61K 45/06* | (2006.01) |
| *A61K 31/192* | (2006.01) |
| *A61K 31/197* | (2006.01) |
| *A61K 31/365* | (2006.01) |
| *A61K 31/40* | (2006.01) |

(Continued)

(52) U.S. Cl.
CPC .......... *A61K 31/7016* (2013.01); *A61K 9/167* (2013.01); *A61K 9/48* (2013.01); *A61K 31/192* (2013.01); *A61K 31/197* (2013.01); *A61K 31/365* (2013.01); *A61K 31/40* (2013.01); *A61K 31/415* (2013.01); *A61K 31/635* (2013.01); *A61K 31/7004* (2013.01); *A61K 31/733* (2013.01); *A61K 33/00* (2013.01); *A61K 45/06* (2013.01)

(58) Field of Classification Search
CPC ....................................................... A61K 9/45
See application file for complete search history.

(56) References Cited

U.S. PATENT DOCUMENTS 4,761,400 A * 8/1988 Doat ................... A61K 9/0056
426/548

OTHER PUBLICATIONS

Smedt et al (Br J Clin Pharmacol, 66:2 (2008) 327-328).*

* cited by examiner

*Primary Examiner* — Benjamin Packard
(74) *Attorney, Agent, or Firm* — Kohn & Associates, PLLC

(57) ABSTRACT

A composition for treating inflammation and pain, including a hydrogen-generating compound in an amount that increases the amount of hydrogen in an individual and has an anti-inflammatory effect. A composition for treating inflammation and pain, including synergistically effective amounts of pregabalin and lactulose. A method of treating inflammation and pain, by administering a composition comprising a hydrogen-generating compound to an individual in an amount that increases the amount of hydrogen in the individual and has an anti-inflammatory effect.

18 Claims, 15 Drawing Sheets

Related U.S. Application Data on Feb. 6, 2012, provisional application No. 61/595,736, filed on Feb. 7, 2012, provisional application No. 61/709,191, filed on Oct. 3, 2012.

(51) Int. Cl.
*A61K 31/635* (2006.01)
*A61K 31/7004* (2006.01)
*A61K 31/733* (2006.01)
*A61K 33/00* (2006.01)
*A61K 9/16* (2006.01)
*A61K 31/415* (2006.01)

Splenda (sucralose)

Equal (aspartame, dextrose and maltodextrin)

Lactulose

D-Galactopyranosyl-β-D-fructofuranose

Inulin

*D-glucopyranosyl-[beta-D-fructofuranosyl]*

ANTI-INFLAMMATORY COMPOUNDS IN COMBINATION WITH HYDROGEN FOR THE TREATMENT OF INFLAMMATION

BACKGROUND OF THE INVENTION

1. Technical Field

The present invention relates to compositions and methods for treating inflammation. More specifically, the present invention relates to anti-inflammatory compounds in combination with hydrogen and hydrogen-generating compounds for treating inflammation.

2. Background Art

There are currently many anti-inflammatory/anti-pain agents that are used to treat inflammation and pain in patients. These agents generally include steroids and non-steroidal anti-inflammatory drugs (NSAIDS). Steroids generally act to reduce inflammation by binding to the glucocorticoid receptor, whereas NSAIDS generally act to inhibit both cyclooxygenase-1 (COX-1) and cyclooxygenase (COX-2), thus inhibiting the catalysis of the formation of the inflammation messengers prostaglandins and thromboxane.

These anti-inflammatory/anti-pain agents are widely used but can have many adverse side effects. Steroids have been shown to cause hyperglycemia, insulin resistance, diabetes, osteoporosis, cataracts, anxiety, depression, colitis, hypertension, ictus, erectile dysfunction, hypogonadism, hypothyroidism, amenorrhea, retinopathy, and teratogenic defects. NSAIDS have been shown to cause gastrointestinal adverse reactions (nausea, dyspepsia, gastric ulceration and bleeding, diarrhea), myocardial infarction, stroke, erectile dysfunction, renal adverse reactions (salt and fluid retention, hypertension, interstitial nephritis, nephrotic syndrome, acute renal failure, acute tubular necrosis), photosensitivity, teratogenic defects, premature birth, miscarriage, raised liver enzymes, headache, dizziness, hyperalaemia, confusion, bronchospasm, rashes, swelling, and irritable bowel syndrome.

One particular anti-inflammation and anti-pain agent that has previously been widely used is gabapentin (NEURONTIN®, Pfizer, Inc.). Gabapentin is a GABA analogue and is indicated for controlling seizures as well as for relieving neuropathic pain. Pain relief is brought about with gabapentin by changing the way in which the body senses pain. More specifically, gabapentin prevents excessive electrical activity in the brain by mimicking the activity of the neurotransmitter GABA. GABA is a natural nerve calming agent, and by mimicking this action, gabapentin can calm nerve activity in the brain.

The successor drug developed to gabapentin was pregabalin (LYRICA®, Pfizer, Inc.). Pregabalin is also a GABA analogue, and is the S-enantiomer of 3-aminomethyl-5-methyl-hexanoic acid. Pregabalin is indicated for neuropathic pain and seizures, and is more specifically indicated for chronic pain disorders such as fibromyalgia. Pregabalin has been preferred over gabapentin due to the fact that it can provide the same efficacy but at much lower doses than are required for gabapentin. Equivalent efficacy at a lower dose can be achieved with pregabalin due to the fact that it has a higher bioavailability and is rapidly absorbed by the body in comparison to gabapentin. Therefore, administering pregabalin can overcome some adverse side effects related to dosing with gabapentin. However, adverse effects can still remain when taking pregabalin, such as commonly reported dizziness or drowsiness, as well as withdrawal effects and other effects as described above.

Therefore, there remains a need for an anti-inflammatory/anti-pain agent that is effective in treating inflammation and pain but reduces the risk of the above adverse reactions.

SUMMARY OF THE INVENTION

The present invention provides for a composition for treating inflammation and pain, including a hydrogen-generating compound in an amount that increases the amount of hydrogen in an individual and has an anti-inflammatory effect.

The present invention also provides for a composition for treating inflammation and pain, including synergistically effective amounts of pregabalin and lactulose.

The present invention provides for a method of treating inflammation and pain, by administering a composition comprising a hydrogen-generating compound to an individual in an amount that increases the amount of hydrogen in the individual and has an anti-inflammatory effect.

DESCRIPTION OF THE DRAWINGS

Other advantages of the present invention are readily appreciated as the same becomes better understood by reference to the following detailed description when considered in connection with the accompanying drawings wherein.

DETAILED DESCRIPTION OF THE INVENTION

Figure 1:
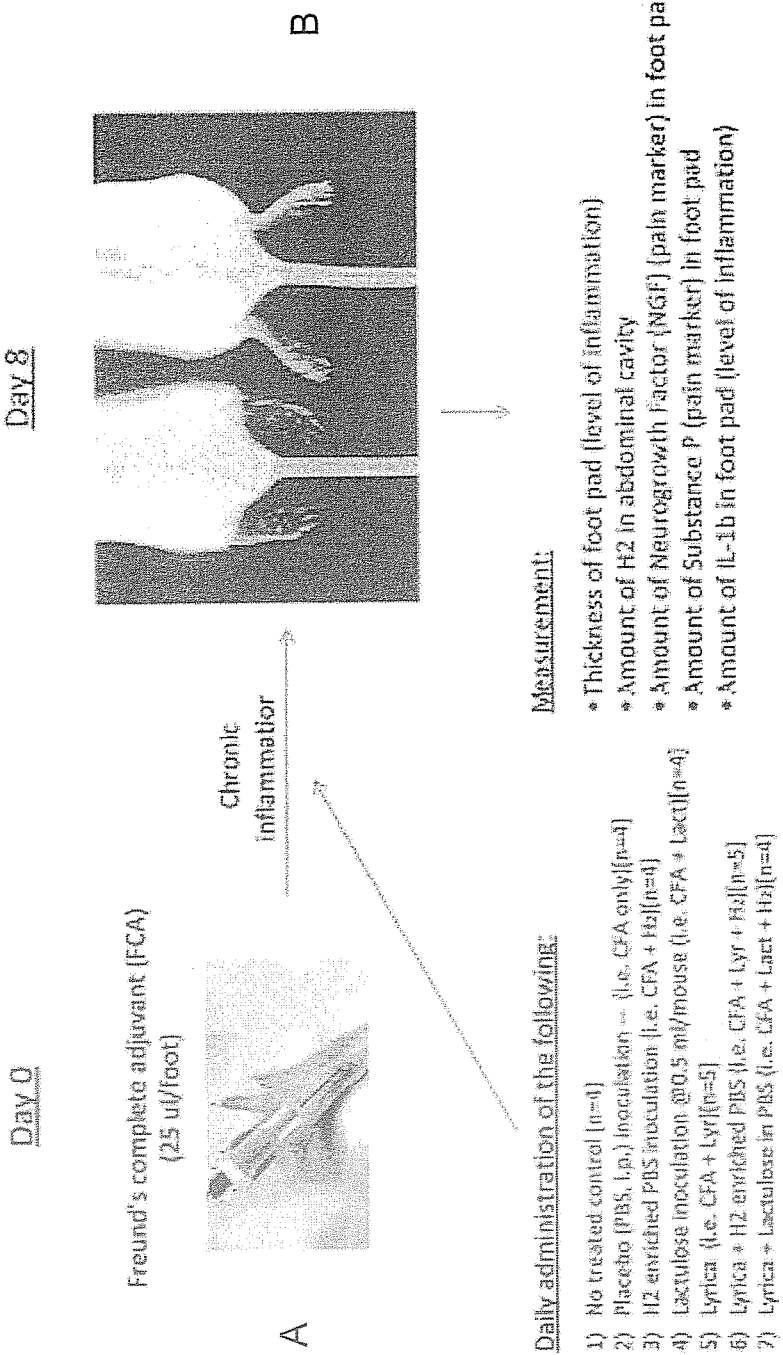
FIG. 1A is a photograph of a foot pad at day 0.
FIG. 1B is a photograph of foot pads at day 8 of administration of the composition of the present invention.

The present invention is generally directed to compositions and methods that are useful for treating inflammation and/or pain. More specifically, the present invention is directed to a composition of an anti-inflammatory or anti-pain agent in combination with a compound that generates increased hydrogen in the body that can be used to treat inflammation and pain.

"Hydrogen" as used herein, refers to the composition H₂ (also written herein as "H2"), but can also include molecular hydrogen (H) and any composition capable of releasing hydrogen. In other words, H2 molecules per se can be administered, a prodrug able to release H2, or a compound that can cause the release of H2 within the body can be administered, as further described below.

The anti-inflammatory or anti-pain agent can be any agent that reduces inflammation and/or treats pain. It should be noted that many of these agents both reduce inflammation and reduce pain; however, some agents can perform only one of these functions as well.

The anti-inflammatory/anti-pain agent can be non-steroidal anti-inflammatory drugs (NSAIDS) such as, but not limited to, acetaminophen, salicylates (aspirin, diflunisal, salsalate), acetic acid derivatives (indomethacin, ketorolac, sulindac etodolac, diclofenac, nabumetone), propionic acid derivatives (ibuprofen, naproxen, flurbiprofen, ketoprofen, oxaprozin, fenoprofen, loxoprofen), fenamic acid derivatives (meclofenamic acid, mefenamic acid, flufenamic acid, tolfenamic acid), oxicam (enolic acid) derivatives (piroxicam, meloxicam, tenoxicam, droxicam, lornoxicam, isoxicam), arylalkanoic acid derivatives (tolmetin); or selective COX-2 inhibitors (celecoxib, rofecoxib, valdecoxib, parecoxib, lumiracoxib, etoricoxib, firocoxib). The anti-inflammatory/anti-pain agent can also be steroids such as, but not limited to, corticosteroids (hydrocortisone, hydrocortisone acetate, cortisone acetate, tixocortol pivalate, prednisolone, methylprednisolone, prednisone, triamcinolone acetonide, triamcinolone alcohol, mometasone, amcinonide, budesonide, desonide, fluocinonide, fluocinolone acetonide, halcinonide, betamethasone, dexamethasone, fluocortolone, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, or fluprednidene acetate). The anti-inflammatory/anti-pain agent can further be immune selective anti-inflammatory derivatives (ImSAIDs) such as, but not limited to, submandibular gland peptide T (SGp-T) and derivatives phenylalanine-glutamine-glycine (FEG) and its D-isomeric form (feG).

Ibuprofen (ADVIL®, Pfizer) is an NSAID that can be used in combination with the hydrogen-generating compound in the present invention. Ibuprofen is generally known as (RS)-2-(4-(2-methylpropyl)phenyl)propanoic acid.

Ibuprofen can be administered in oral form in doses of 200 to 3200 mg/day; however, due to synergism with the hydrogen-generating compound, a lower dose can be preferred and normal side effects experienced can be reduced or eliminated. Any other administration methods as described herein can also be used. Administration of Ibuprofen in combination with H2 or lactulose is shown to reduce inflammation in a greater amount than administration of Ibuprofen alone, as shown in Examples 3 and 4 below.

Celecoxib (CELEBREX®, GD Searle) is another particular NSAID that can be used in combination with the hydrogen-generating compound in the present invention. Celecoxib is generally described in U.S. Pat. No. 5,466,823 to Talley, et al. Briefly, celecoxib is a compound that is useful in treating inflammation-related disorders defined by Formula I:

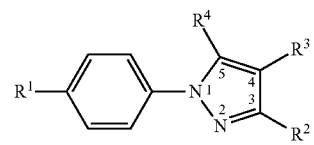
(Formula I)

wherein $R^1$ is selected from sulfamyl, halo, alkyl, alkoxy, hydroxyl and haloalkyl; wherein $R^2$ is selected from hydrido, halo, haloalkyl, cyano, nitro, formyl, carboxyl, alkoxycarbonyl, carboxyalkyl, alkoxycarbonylalkyl, amidino, cyanoamidino, amido, alkoxy, amidoalkyl, N-monoalkylamido, N-monoarylamido, N,N-dialkylamido, N-alkyl-N-arylamido, alkylcarbonyl, alkylcarbonylalkyl, hydroxyalkyl, alkylthio, alkylsulfinyl, alkylsulfonyl, N-alkylsulfamyl, N-arylsulfamyl, arylsulfonyl, N,N-dialkylsulfamyl, N-alkyl-N-arylsulfamyl and heterocyclic; wherein $R^3$ is selected from hydrido, halo, haloalkyl, cyano, nitro, formyl, carboxyl, alkoxycarbonyl, carboxyalkyl, alkoxycarbonylalkyl, amidino, cyanoamidino, amido, alkoxy, amidoalkyl, N-monoalkylamido, N-monoarylamido, N,N-dialkylamido, N-alkyl-N-arylamido, alkylcarbonyl, alkylcarbonylalkyl, hydroxyalkyl, alkylthio, alkylsulfinyl, alkylsulfonyl, N-alkylsulfamyl, N-arylsulfamyl, arylsulfonyl, N,N-dialkylsulfamyl, N-alkyl-N-arylsulfamyl, heterocyclic, heterocycloalkyl and aralkyl; wherein $R^4$ is selected from aryl, cycloalkyl, cycloalkenyl and heterocyclic; wherein $R^4$ is optionally substituted at a substitutable position with one or more radicals selected from halo, alkylthio, alkylsulfinyl, alkyl, alkylsulfonyl, cyano, carboxyl, alkoxycarbonyl, amido, N-monoalkylamido, N-monoarylamido, N,N-dialkylamido, N-alkyl-N-arylamido, haloalkyl, hydroxyl, alkoxy hydroxyalkyl haloalkoxy, sulfamyl, N-alkylsulfamyl, amino, N-alkylamino, N,N-dialkylamino, heterocyclic, nitro and acylamino; or wherein $R^3$ and $R^4$ together form

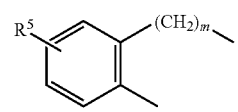

and m is 1 to 3, inclusive; and wherein $R^5$ is one or more radicals selected from halo, alkylthio, alkylsulfinyl, alkylsulfonyl, cyano, carboxyl, alkoxycarbonyl, amido, N-monoalkylamido, N-monoarylamido, alkyl, N,N-dialkylamido, N-alkyl-N-arylamido, haloalkyl, hydrido, hydroxyl, alkoxy, hydroxyalkyl, haloalkoxy, sulfamyl, N-alkylsulfamyl, amino, alkylamino, heterocyclic, nitro and acylamino; provided $R^2$ and $R^3$ are not identical radicals selected from hydrido, carboxyl and ethoxycarbonyl; further provided that $R^2$ cannot be carboxyl when $R^3$ is hydrido and when $R^4$ is phenyl; and further provided that $R^4$ is sulfamyl or N-alkylsulfamyl when $R^1$ is halo; or a pharmaceutically-acceptable salt thereof.

Celecoxib can be administered in oral form in doses of 50 to 400 mg/day; however, due to synergism with the hydrogen-generating compound, a lower dose can be preferred and normal side effects experienced can be reduced or eliminated. Any other administration methods as described herein can also be used. Administration of celecoxib in combination with H2 or lactulose is shown to reduce inflammation in a greater amount than administration of celecoxib alone, as shown in Examples 3 and 4 below.

Rofecoxib (VIOXX®, Merck) is another particular NSAID that can be used in combination with the hydrogen-generating compound in the present invention. Rofecoxib is generally described in U.S. Pat. No. 5,474,995 to Ducharme, et al. and U.S. Pat. No. 5,691,374 to Black, et al. Briefly, the rofecoxib compound of Formula II

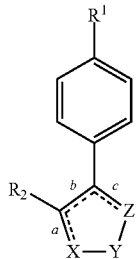

(Formula II)

or pharmaceutically acceptable salts thereof is useful in the treatment of cyclooxygenase-2 mediated diseases, wherein: X—Y—Z is selected from the group consisting of:
  (a) —CH$_2$CH$_2$CH$_2$—,
  (b) —C(O)CH$_2$CH$_2$—,
  (c) —CH$_2$CH$_2$C(O)—,
  (d) —CR$^5$(R$^5$)—O—C(O)—,
  (e) —C(O)—O—CR$^5$(R$^{5'}$)—,
  (f) —CH$_2$—NR$^3$—CH$_2$—,
  (g) —CR$^5$(R$^{5'}$)—NR$^3$—C(O)—,
  (h) —CR$^4$=CR$^{4'}$—S—,
  (i) —S—CR$^4$=CR$^{4'}$—,
  (j) —S—N=CH—,
  (k) —CH=N—S—,
  (l) —N=CR$^4$—O—,
  (m) —O—CR4=N—,
  (n) —N=CR$^4$—NH—;
  (o) —N=CR$^4$—S—, and
  (p) —S—CR$^4$—N—;
  (q) —C(O)—NR$^3$—CR$^5$(R$^5$)—;
  (r) —R$^3$N—CH=CH— provided R$^1$ is not —S(O)$_2$Me
  (s) —CH=CH—NR$^3$— provided R$^1$ is not —S(O)$_2$Me
when side b is a double bond, and sides a an c are single bonds; and
X—Y—Z— is selected from the group consisting of:
  (a) =CH—O—CH=, and
  (b) =CH—NR$^3$—CH=,
  (c) =N—S—CH=,
  (d) =CH—S—N=,
  (e) =N—O—CH=,
  (f) =CH—O—N=,
  (g) =N—S—N=,
  (h) =N—O—N=,
when sides a and c are double bonds and side b is a single bond;
R$^1$ is selected from the group consisting of
  (a) S(O)$_2$CH$_3$,
  (b) S(O)$_2$NH$_2$,
  (c) S(O)$_2$NHC(O)CF$_3$,
  (d) S(O)(NH)CH$_3$,
  (e) S(O)(NH)NH$_2$,
  (f) S(O)(NH)NHC(O)CF$_3$,
  (g) P(O)(CH$_3$)OH, and
  (h) P(O)(CH$_3$)NH$_2$,
R$^2$ is selected from the group consisting of
  (a) C$_{1-6}$ alkyl,
  (b) C$_3$, C$_4$, C$_5$, C$_6$, and C$_7$, cycloalkyl, (c) mono-, di- or tri-substituted phenyl or naphthyl wherein the substituent is selected from the group consisting of
    (1) hydrogen,
    (2) halo,
    (3) C$_{1-6}$ alkoxy,
    (4) C$_{1-6}$ alkylthio,
    (5) CN,
    (6) CF$_3$,
    (7) C$_{1-6}$ alkyl,
    (8) N$_3$,
    (9) —CO$_2$H,
    (10) —CO$_2$—C$_{1-4}$ alkyl,
    (11) —C(R$^5$)(R$^6$)—OH,
    (12) —C(R$^5$)(R$^6$)—O—C$_{1-4}$ alkyl, and
    (13) —C$_{1-6}$ alkyl-CO$_2$—R$^5$;
  (d) mono-, di- or tri-substituted heteroaryl wherein the heteroaryl is a monocyclic aromatic ting of 5 atoms, said ting having one hetero atom which is S, O, or N, and optionally 1, 2, or 3 additionally N atoms; or
the heteroaryl is a monocyclic ring of 6 atoms, said ring having one hetero atom which is N, and optionally 1, 2, 3, or 4 additional N atoms; said substituents are selected from the group consisting of
    (1) hydrogen,
    (2) halo, including fluoro, chloro, bromo and iodo,
    (3) C$_{1-6}$ alkyl,
    (4) C$_{1-6}$ alkoxy,
    (5) C$_{1-6}$ alkylthio,
    (6) CN,
    (7) CF$_3$,
    (8) N$_3$,
    (9) —C(R$^5$)(R$^6$)—OH, and
    (10) —C(R$^5$)(R$^6$)—O—C$_{1-4}$ alkyl;
  (e) benzoheteroaryl which includes the benzo fused analogs of (d);
R$^3$ is selected from the group consisting of
  (a) hydrogen,
  (b) CF$_3$,
  (c) CN,
  (d) C$_{1-6}$ alkyl,
  (e) hydroxy C$_{1-6}$ alkyl,
  (f) —C(O)—C$_{1-6}$ alkyl,
  (g) optionally substituted
    (1) —C$_{1-6}$ alkyl-Q,
    (2) —C$_{1-3}$ alkyl-O—C$_{1-3}$ alkyl-Q,
    (3) —C$_{1-3}$ alkyl-S—C$_{1-3}$ alkyl-Q,
    (4) —C$_{1-5}$ alkyl-O-Q, or
    (5) —C$_{1-5}$ alkyl-S-Q,
  wherein the substituent resides on the alkyl and the substituent is C$_{1-3}$ alkyl;
  (h) -Q
R$^4$ and R$^{4'}$ are each independently selected from the group consisting of
  (a) hydrogen,
  (b) CF$_3$,
  (c) CN,
  (d) C$_{1-6}$ alkyl,
  (e) -Q,
  (f) —O-Q;
  (g) —S-Q, and
  (h) optionally substituted
    (1) —C$_{1-6}$ alkyl-Q,
    (2) —O—C$_{1-5}$ alkyl-Q,
    (3) —S—C$_{1-5}$ alkyl-Q,
    (4) —C$_{1-3}$ alkyl-O—C$_{1-3}$ alkyl-Q,
    (5) —C$_{1-3}$ alkyl-S—C$_{1-3}$ alkyl-Q, (6) —$C_{1-6}$ alkyl-O-Q, (7) —$C_{1-6}$ alkyl-S-Q, wherein the substituent resides on the alkyl and the substituent is $C_{1-3}$ alkyl, and $R^5$, $R^{5'}$, $R^6$, $R^7$ and $R^8$ are each independently selected from the group consisting of (a) hydrogen, (b) $C_{1-6}$ alkyl, or $R^5$ and $R^6$ or $R^7$ and $R^8$ together with the carbon to which they are attached form a saturated monocyclic carbon ring of 3, 4, 5, 6 or 7 atoms;

Q is $CO_2H$, $CO_2$—$C_{1-4}$ alkyl, tetrazolyl-5-yl, $C(R7)(R^8)$(OH), or $C(R^7)(R^8)(O$—$C_{1-4}$ alkyl);

provided that when X—Y—Z is —S—$CR^4$=$CR^{4'}$, then $R^4$ and $R^{4'}$ are other than $CF_3$.

Rofecoxib can be administered in oral form in doses of 12.5 to 50 mg/day; however, due to synergism with the hydrogen-generating compound, a lower dose can be preferred and normal side effects experienced can be reduced or eliminated. Any other administration methods as described herein can also be used.

The anti-inflammatory/anti-pain agent can also be a narcotic composition such as, but not limited to, buprenorphine, butorphanol, codeine, hydrocodone, hydromorphone, levorphail, meperidine, methadone, morphine, nalbuphine, oxycodone, oxymorphone, pentaxocine, or propoxyphene.

The anti-inflammatory/anti-pain agent can also be other analgesic compositions such as, but not limited to, tramadol, or capsaicin. The anti-inflammatory/anti-pain agent can also be a topical anesthetic, such as, but not limited to, benzocaine, dibucaine, lidocaine, or prilocaine.

The anti-inflammatory/anti-pain agent can also be any suitable biologic agent that reduces inflammation and/or pain, such as etanercept (ENBREL®, Amgen, Inc.). Etanercept reduces the levels of inflammatory-causing tumor necrosis factor (TNF) in the body and is administered by injection. Other biologic agents that inhibit IL-1 or TNF, or that effect other biologic pathways, can also be used, such as, but not limited to, adalimumab (HUMIRA®, Abbott), anakinra (KINERET®, Amgen, Inc.), infliximab (REMICADE®, Janssen Biotech, Inc.), certolizumab-pegol (CIMZIA®, UCB, Inc.), and Natalizumab (TYSABRI®, Biogen Idec).

The anti-inflammatory/anti-pain agent can further be any combination of the above compositions along with other agents. Some readily available combinations of anti-inflammatory/anti-pain agents are as follows: butalbital, acetameniphen, and caffeine; butalbital, aspirin, and caffeine; butalbital, acetaminophen, caffeine, and codeine; hydrocodone and ibuprofen; pentazocine and naloxone; acetaminophen and codeine; dihydrocodeine, acetaminophen, and caffeine; hydrocodone and acetaminophen; oxycodone and acetaminophen; pentazocine and acetaminophen; propoxyphene and acetaminophen; aspirin, caffeine, and dihydrocodeine; aspirin and codeine; hydrocodone and aspirin; oxycodone and aspirin; pentazocine and aspirin; and propoxyphene, aspirin, and caffeine.

Most preferably, the anti-inflammatory/anti-pain agent is pregabalin (LYRICA®, Pfizer). Pregabalin is currently indicated for the treatment of neuropathic pain, seizures, fibromyalgia, and generalized anxiety disorder. Pregabalin and the method of making pregabalin are described in U.S. Pat. No. 5,847,151. Pregabalin can be administered in oral form in doses of 25 to 600 mg/day; however, due to synergism with the hydrogen-generating compound, a lower dose can be preferred. Any other administration methods as described herein can also be used.

Briefly, pregabalin is a series of 3-alkyl-4-aminobutyric acid or 3-alkyl glutamic acid analogs. Most preferably, pregabalin is the S-enantiomer of 3-(aminomethyl)-5-methyl-hexanoic acid. However, other analogs as discussed herein can also be used and salts of any other analogs can be used. Illustrative of the alkyl moieties as represented by $R_1$ and $R_{11}$ in Formulas III and IV are methyl, ethyl, propyl, isopropyl, n-butyl, isobutyl, sec-butyl, tert-butyl, isopentyl, and neopentyl as well as other alkyl groups. The cycloalkyl groups represented by $R_1$ and $R_{11}$ in Formulas III and IV are exemplified by cyclopropyl, cyclobutyl, cyclopentyl, and cyclohexyl.

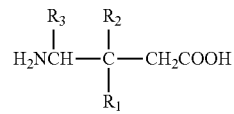
(Formula III)

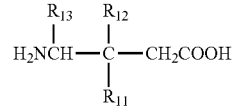
(Formula IV)

The more preferred compounds of pregabalin of the present invention are of Formula III above wherein $R_3$ is hydrogen, $R_2$ is hydrogen, and $R_1$ is isobutyl. That is, the preferred compound is 4-amino-3-(2-methylpropyl)butanoic acid. It has been found that this compound is unexpectedly more potent than the other analogs synthesized and tested in vivo. What is further surprising, is that this preferred compound has been found to be the least effective one of the analogs tested in activating GAD in vitro. Accordingly, it was very unexpected that this preferred compound had such a high potency when tested in vivo.

The more preferred compounds of pregabalin of the present invention are the (S)-(+)- and the (R)(−)-4-amino-3-(2-methylpropyl)butanoic acid with the (S)-(+)-enantiomer being most preferred. The (S)-(+)-enantiomer was found to be the most potent compound within the scope of the present invention for displacement of tritiated gabapentin, and both the (S)-(+)- and the (R)-(−)-enantiomers showed pronounced stereoselectivity for both displacement of tritiated gabapentin and for anticonvulsant activity in vivo.

The pregabalin compounds made in accordance with the present invention can form pharmaceutically acceptable salts with both organic and inorganic acids or bases. For example, the acid addition salts of the basic compounds are prepared either by dissolving the free base in aqueous or aqueous alcohol solution or other suitable solvents containing the appropriate acid and isolating the salt by evaporating the solution. Examples of pharmaceutically acceptable salts are hydrochlorides, hydrobromide, hydrosulfates, etc, as well as sodium, potassium, and magnesium, etc, salts.

The method for the formation of the 3-alkyl-4-aminobutanoic acids starting from 2-alkanoic esters is prepared from commercially available aldehydes and monomethyl malonate by the Knoevenagel reaction, (Kim Y. C., et al, J. Med. Chem. 1965:8509) with the exception of ethyl 4,4-dimethyl-2-pentenoate.

More specifically, the following is a procedure that can be generally applied to the preparation of all the 3-alkylglutamic acids. Ten grams of a 3-alkyl-5,5-dicarbethoxy-2-pyrrolidinone was refluxed in 150 mL of 49% fuming HBr for 4 hours. After this time, the contents were placed in an evaporator and the volatile constituents were removed in vacuo with the aid of a hot-water bath. The gummy residue was dissolved in 25 mL of distilled water and the water was removed with the aid of the evaporator. This process was repeated once more. The residue was dissolved in 20 mL of water, and the pH of the solution was adjusted to 3.2 with concentrated $NH_3$ solution. At this point the chain length of the individual 3-alkylglutamic acids altered the solubility so that those whose side chains were larger precipitated with the ease from solution. Precipitation of the alkylglutamic acids with smaller substituents (methyl, ethyl, and propyl) could be encouraged by cooling on an ice bath or by diluting the aqueous solution with 100 mL of absolute ethanol. Precipitation from the water-alcohol mixture is complete in 48 hours. Care must be taken to add the ethanol slowly to prevent the precipitation of an amorphous solid that is not characteristic of the desired 3-alkylglutamic acids. Samples of the amino acids were purified for analysis by recrystallizing from a water-ethanol mixture. All melted with decomposition. Melting points of the decomposed 3-alkylglutamic acids corresponded with those of their pyroglutamic acids.

Ethyl 4,4-dimethyl-2-pentenoate was prepared from 2,2-dimethylpropanol and ethyl lithioacetate, followed by dehydration of the β-hydroxy ester with phosphoryl chloride and pyridine.

The Michael addition of nitromethane to α,β-unsaturated compounds mediated by 1,1,3,3-tetramethylguanidine or 1,8-diazabicyclo-[5.4.0]undec-7-ene(DBU) afforded 4-nitroesters in good yields. More specifically, a mixture of nitromethane (5 mol), α,β-unsaturated ester (1 mol), and tetramethyl-guanidine (0.2 mol) was stirred at room temperature for 2 to 4 days. (In case of methyl acrylate, the ester has to be added at a temperature below 300.) The progress of the reaction was followed by IR (disappearance of the C=C band) and G. L. C. analysis. The reaction mixture was washed with dilute hydrochloric acid and extracted with ether. The organic extract was dried, the solvent removed at reduced pressure, and the 20 residue distilled at a pressure of 2 torr. Although the aliphatic nitro compounds are usually reduced by either high pressure catalytic hydrogenation by metal-catalyzed transfer hydrogenation, or by newly introduced hydrogenolysis methods with ammonium formate or sodium borohydride and palladium as catalysts, applicants have found that 4-nitrocarboxylic esters can be reduced almost quantitatively to the corresponding 4-aminocarboxylic esters by hydrogenation using 10% palladium on carbon as catalysts in acetic acid at room temperature and atmospheric pressure. The amino esters produced were subjected to acid hydrolysis to afford the subject inventive compounds in good yields. This procedure provides access to a variety of 3-alkyl-4-aminobutanoic acids as listed in Tables 1 and 2 as examples and thus is advantageous in comparison to methods previously used.

TABLE 1

Activation of GAD by GABA analogs at various concentrations expressed in %

$$H_3N^+CH_2C(R_1)(R_2)CH_2COO^-$$

| $R_1, R_2$ | 2.5 mM | 1.0 mM | 0.5 mM | 0.25 mM | 0.1 mM | 0.05 mM |
|---|---|---|---|---|---|---|
| (R,S)-$CH_3$, H | 239 | 168 | 142 | 128 | 118 | 107 |
| (R)-$CH_3$H | 327 | 202 | 185 | 135 | 128 | 109 |
| (S)-$CH_3$H | 170 | 118 | — | 103 | — | — |
| $CH_3$, $CH_3$ | 174 | 125 | — | 109 | — | — |
| (R,S)-$C_2H_5$, H | 172 | 128 | — | 108 | — | — |
| (R,S)-n-$C_3H_7$, H | 156 | 112 | — | 105 | — | — |
| (R,S)-i-$C_3H_7$, H | 140 | 108 | — | 104 | — | — |
| (R,S)-n-$C_4H_9$, H | 178 | 117 | — | 108 | — | — |
| (R,S)-i-$C_4H_9$, H | 143 | 113 | — | 109 | — | — |
| (R,S)-s-$C_4H_9$, H | 169 | 119 | — | 105 | — | — |
| (R,S)-t-$C_4H_9$, H | 295 | 174 | 147 | 121 | 117 | 108 |
| (R,S)-neo-$C_5H_{11}$, H | 279 | 181 | — | 130 | — | — |
| (R,S)-i-$C_5H_{11}$, H | 142 | 118 | — | 109 | — | — |
| (R,S)-$C_6H_{13}$, H | 125 | 100 | — | 100 | — | — |
| (R,S)-$C_6H_5$, H | 218 | 129 | — | 110 | — | — |

$$H_3NCHCH(R)CH_2COO^-$$ with $CH_3$ on N

| R | 2.5 mM | 1.0 mM | 0.5 mM | 0.25 mM | 0.1 mM | 0.05 mM |
|---|---|---|---|---|---|---|
| H(R,S) | 140 | 111 | — | 104 | — | — |
| H(R) | 173 | 125 | — | 108 | — | — |
| H(S) | 100 | 100 | — | 100 | — | — |
| $CH_3$ | 143 | 121 | — | 109 | — | — |
| $C_6H_5$ | 207 | 151 | — | 112 | — | — |
| Sodium Valproate | 207 | 138 | 124 | 119 | 115 | 105 |
| GABAPENTIN | 178 | 145 | — | 105 | — | — |

Activation of GAD by glutamate analogs expressed in %

$$H_3N^+-CH(COO^-)-CH(R)-CH_2-COOH$$

| R | 2.5 mM | 1.0 mM | 0.25 mM |
|---|---|---|---|
| $CH_3$ | 212 | 144 | 113 |
| $C_2H_5$ | 170 | 128 | 113 |
| n-$C_3H_7$ | 153 | 125 | 108 |
| i-$C_3H_7$ | 144 | 114 | 105 |
| n-$C_4H_9$ | 133 | 117 | 105 |
| i-$C_4H_9$ | 129 | 112 | 106 |
| $C_6H_5$ | 172 | 135 | 112 |
| Sodium Valproate | 207 | 138 | 119 |

TABLE 2

Prevention of tonic extensor seizures in mice following intravenous administration of 3-substituted GABA derivatives

| R | Dose (mg/kg) | Time After Dose (min) | Effect # Protected/# Tested | Ataxia # Ataxia/# Tested |
|---|---|---|---|---|
| (R,S)—$CH_3$ | 10 | 120 | 0/5 | 0/5 |
| | 30 | 120 | 4/5 | 0/5 |
| | 100 | 120 | 3/5 | 0/5 |
| $CH_3$ | 1 | 120 | 1/10 | 0/10 |
| | 3 | 120 | 2/10 | 0/10 |
| | 10 | 120 | 4/10 | 0/10 |
| | 30 | 120 | 3/10 | 0/10 |
| | 100 | 120 | 3/10(5/10) | 1/10 |
| $CH_3$ | 10 | 120 | 1/10 | 1/10 |
| | 30 | 120 | 2/10 | 0/10 |
| | 100 | 120 | 5/10 | 0/10 |
| t-$C_4H_9$ | 10 | 120 | 2/10 | 0/10 |
| | 30 | 120 | 2/10 | 0/10 |
| | 100 | 120 | 5/10 | 0/10 |
| $C_2H_5$ | 3 | 120 | 1/5 | 0/5 |
| | 10 | 120 | 1/5 | 0/5 |
| | 30 | 120 | 2/5 | 0/5 |
| | 100 | 120 | 5/5 | 0/5 |
| $(CH_3)_2$ | 30 | 120 | 4/5 | 0/5 |
| | 100 | 120 | 4/5 | 0/5 |
| n-$C_4H_9$ | 10 | 120 | 1/10 | 0/10 |
| | 30 | 120 | 3/10 | 0/10 |
| | 100 | 120 | 4/10 | 0/10 |

TABLE 2-continued

Prevention of tonic extensor seizures in mice following intravenous administration of 3-substituted GABA derivatives

| R | Dose (mg/kg) | Time After Dose (min) | Effect # Protected/# Tested | Ataxia # Ataxia/# Tested |
|---|---|---|---|---|
| s-$C_4H_9$ | 3 | 120 | 2/10 | 0/10 |
| | 10 | 120 | 3/10 | 0/10 |
| | 30 | 120 | 2/10 | 0/10 |
| i-$C_4H_9$ | 0.3 | 120 | 1/10 | 0/10 |
| | 0.8 | 120 | 3/10 | 0/10 |
| | 2.0 | 120 | 5/10 | 0/10 |
| | 5.5 | 120 | 7/10 | 0/10 |
| | 14.4 | 120 | 9/10 | 0/10 |
| n-$C_3H_7$ | 3 | 120 | 2/10 | 0/10 |
| | 10 | 120 | 2/10 | 3/10 |
| | 100 | 120 | 3/10 | 0/10 |
| i-$C_3H_7$ | 10 | 120 | 5/10 | 1/10 |
| | 30 | 120 | 5/10 | 0/10 |
| | 100 | 120 | 6/10 | 0/10 |
| $C_6H_5$ | 100 | 120 | 0/10 | 0/10 |
| neo-$C_5H_{11}$ | 10 | 120 | 2/10 | 0/10 |
| | 30 | 120 | 4/10 | 0/10 |
| | 100 | 120 | 4/10 | 0/10 |

High-intensity corneal electroshock consisted of 50 mA, base-to-peak sinusoidal current for 0.2 seconds. All other data was from low-intensity electroshock, 17 mA base-to-peak sinusoidal current for 0.2 seconds.

Examples of more specific methods of making compounds in accordance with the present invention are as follows, optionally utilizing the methods described in detail above. When the starting material is not commercially available, the synthetic sequence may be initiated with the corresponding alcohol, which is oxidized to the aldehyde by the method of Corey E. J., et al, Tetrahedron Lett. 1975: 2647-2650.

The chiral compounds of Formulas III and IV are prepared as set forth in the schematic in Chart I hereof. Although the schematic in Chart I depicts the chiral synthesis of specific compound (S)-(+)-4-amino-3-(2-methylpropyl)butanoic acid, one skilled in the art can readily see that the method of synthesis can be applied to any diastereomeric compound of Formulas III and IV.

CHART 1

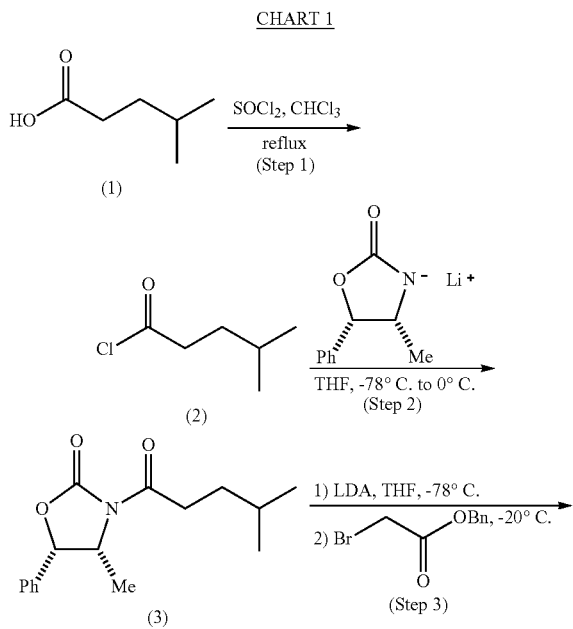

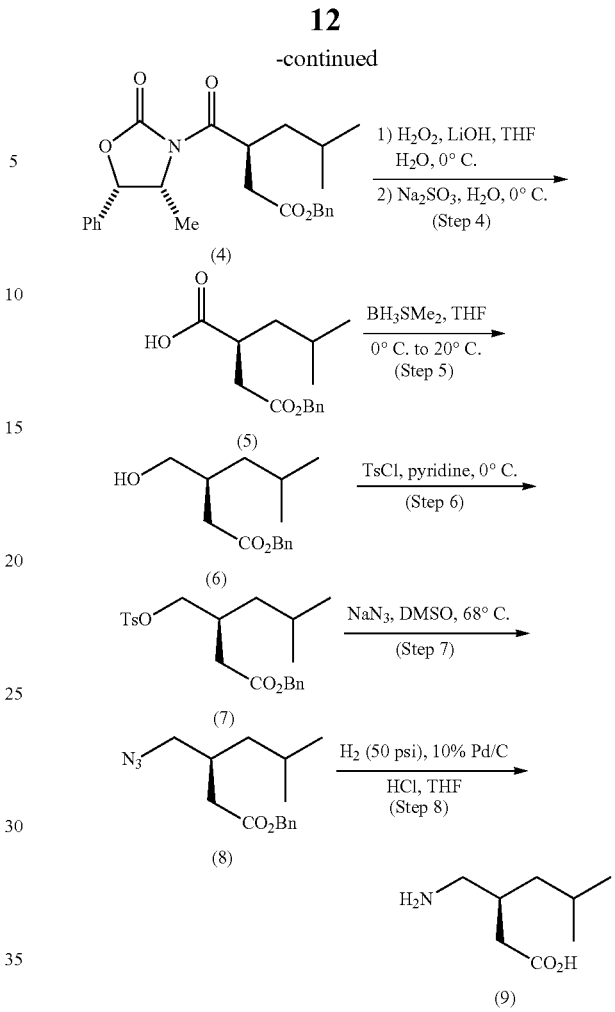

In Chart I Ph is phenyl, Bn is benzyl, THF is tetrahydrofuran, LDA is lithium diisopropylamide, $BH_3SMe_2$ is borane dimethyl sulfide complex, TsCl is tosyl chloride, and DMSO is dimethylsulfoxide.

The detailed synthetic procedure is set forth herein below in Example 1. The key introductory literature for this methodology was discussed in Evans' paper, J. Am. Chem. Soc. 1982; 104:1737-9. The metal enolate can be formed with a lithium or sodium amide base, and subsequently alkylated to give a substituted carboxylic acid derivative. This methodology was valuable for the enantioselective synthesis of these α-substituted carboxylic acid derivatives. In this seminal paper, Evans described the preparation of propionic acid derivatives with a series of simple alkylating agents. By varying the stereochemistry of the chiral synthon (the oxazolidinone), he was able to get high stereoselectivity.

Evans has used this chiral auxiliary in other synthetic studies, but none has been related to 4-amino-3-(2-methylpropyl)butanoic acid which contains a β-substituted-γ-amino acid. The methodology as presented by Evans teaches toward α-substitution, and away from β-substitution, and has not been used in the preparation of this type of unusual amino acid. N-acyloxazolidinones have been used to form chlorotitanium enolates that have been reacted with Michael adducts such as acrylonitrile, J. Org. Chem. 1991; 56:5750-2. They have been used in the synthesis of the rutamycin family of antibiotics, J. Org. Chem. 1990; 55:6260-8 and in stereoselective aldol condensations, Org. Synth. 1990; 68:83-91. Chiral α-amino acids were prepared via the oxazolidinone approach. In this sequence, a dibutylboron enolate was brominated and displaced with azide, Tetrahedron Lett. 1987; 28:1123-6. Other syntheses of β-hydroxy-α-amino acids were also reported via this chiral auxiliary through aldol condensation (Tetrahedron Lett. 1987; 28:39-42; J. Am. Chem. Soc. 1987; 109:7151-7). α,β-Unsaturated N-acyloxazolidinones have also been used to induce chirality in the Diels-Alder reaction, (J. Am. Chem, Soc. 1988; 110:1238-56. In none of these examples, or others found in the literature, is this methodology used to prepare (β-substituted carboxylic acids or 3-substituted GABA analogs.

The chiral compounds of Formulas III and IV can also be prepared in a manner which is similar to the synthesis depicted in Chart I. In this embodiment, however, step 8 in Chart I is replaced by an alternate two-step procedure (sodium hydroxide is preferred, however, other solvents known to those of skill in the art which can hydrolyze the azide (8) to intermediate azide (8a) can be employed). Instead of reducing the azide (8) to the amino acid (9) in Chart I, the alternate procedure hydrolyzes the azide (8) to give an intermediate azide (8a) which is subsequently reduced (see Chart Ia).

CHART Ia

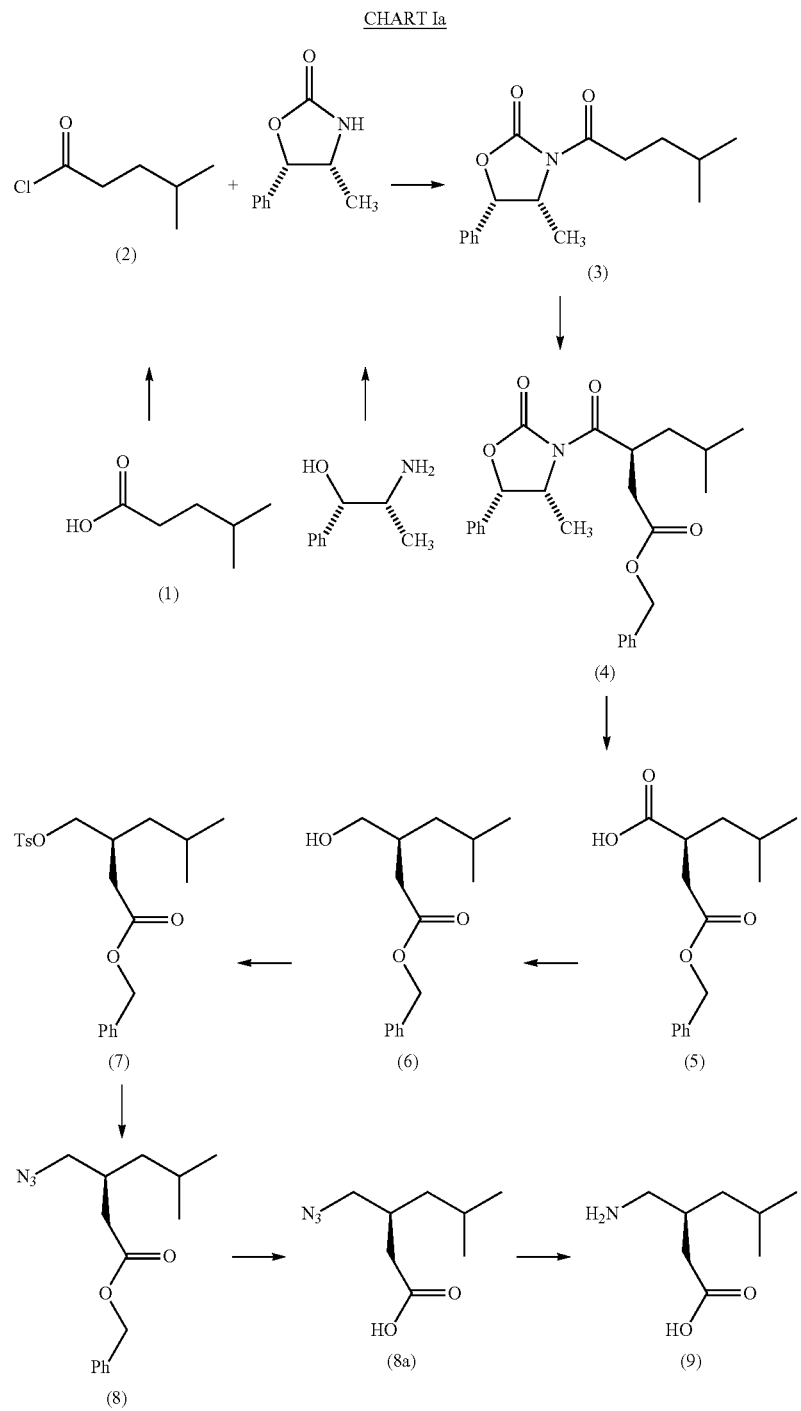

There are two major advantages to hydrolyzing azide (8) to give the intermediate azide (8a) prior to reduction. The first advantage is that intermediate azide (8a) may be purified by extraction into aqueous base. After the aqueous extract is acidified, intermediate azide (8a) may be extracted into the organic phase and isolated. This allows for a purification of intermediate azide (8a) which does not involve chromatography. The purification of azide (8) requires chromatography which is very expensive and often impractical on a large scale.

The second advantage is that intermediate azide (8a) may be reduced to amino acid (9) without added acid. Reduction of azide (8) requires addition of acid, e.g., hydrochloric acid in order to obtain amino acid (9). Unfortunately, lactamization of amino acid (9) is promoted by the presence of acid. Intermediate azide (8a) may be reduced under near neutral conditions to give amino acid (9), thus minimizing the problem of lactam formation.

In another preferred embodiment, the chiral compounds of Formulas III and IV can be prepared as set forth in the Schematic in Chart II hereof. Although the schematic in Chart II depicts the chiral synthesis of specific compound (S)-(+)-4-amino-3-(2-methyl-propyl)butanoic acid, one skilled in the art can readily see that the method of synthesis can be applied to any diastereomeric compound of Formulas III and IV.

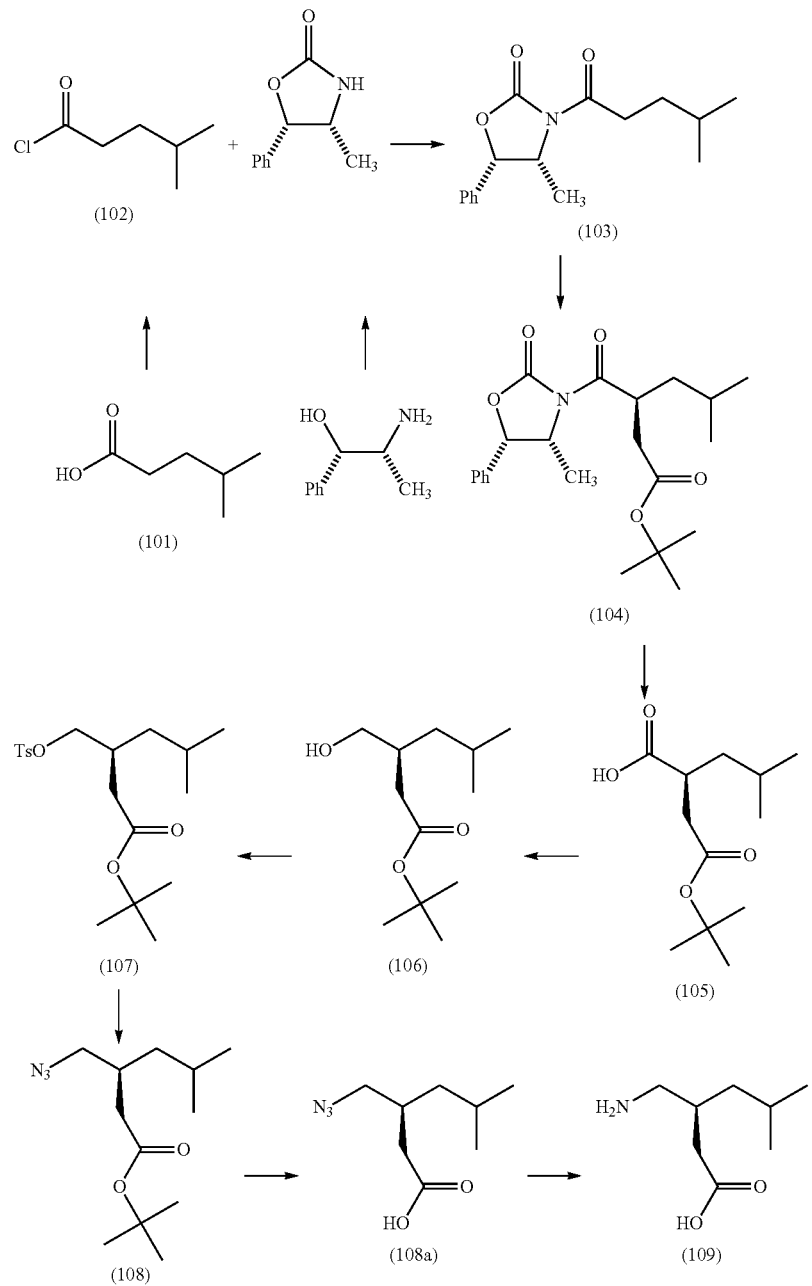

In Chart II Ph is phenyl, and Ts is tosyl.

Another synthetic procedure is similar to the synthesis route depicted in Chart I, however, the procedure of Chart II replaces the benzyl ester in the synthesis route of Chart I with a t-butyl ester. The desired amino acid (9) and (109) is the same end product in both Charts I and II, respectively. There are several advantages to using the t-butyl ester rather than the benzyl ester in the synthesis of amino acid (9) or (109). A first advantage relates to the hydrolysis of the chiral auxiliary in step 4 of Chart 1. During the hydrolysis of the chiral auxiliary in this reaction some hydrolysis of the benzyl ester often occurs. Hydrolysis of the t-butyl ester in Chart II has not been experienced.

Another advantage relates to the use of alcohol (106) in Chart II over the use of alcohol (6) in Chart I. A problem with the benzyl ester-alcohol is the tendency of the benzyl ester-alcohol to undergo lactonization as shown below. Although lactonization of the benzyl ester can be avoided under some conditions, the t-butyl ester-alcohol is far less prone to lactonization.

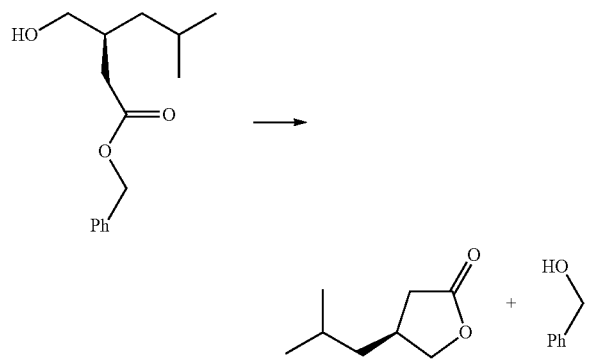

Still another advantage, which was previously discussed with regard to the synthetic procedure depicted by Chart Ia, is that the t-butyl synthetic route minimizes the problem of lactam formation of the amino acid end product (109).

4-methyl-5-phenyl-2-oxazolidinone, 4-methyl-(2-methyl-propyl)-2-dioxo-5-phenyl-3-oxazolidine butanoic acid, phenylmethyl ester, 4-methyl-pentanoyl chloride, 4-methyl-3-(4-methyl-1-oxopentyl)-5-phenyl-2-oxazolidinone, 2-(2-methylpropyl)-butanedioic acid, 4-(phenylmethyl)ester, 3-(azidomethyl)-5-methyl-hexanoic acid, phenylmethyl ester, 3-(hydroxymethyl)-5-methyl-hexanoic acid, phenylmethyl ester, 5-methyl-3-[[[(4-methylphenyl)sulfonyl]oxy]-methyl]-hexanoic acid, phenylmethyl ester, 3-(azidomethyl)-5-methyl-hexanoic acid, 2-(2-methylpropyl)-1,4-butanedioic acid, 4-(1,1-dimethylethyl) ester, 3-(azidomethyl)-5-methyl-, 1,1-dimethylethyl ester, 3-(hydroxymethyl)-5-methyl-hexanoic acid, 1,1-dimethyl ester, 5-methyl-3-[[[(4-methyl(phenyl)sulfonyl]oxy]-methyl-hexanoic acid, 1,1-dimethylethyl ester, or 4-methyl-(2-methylpropyl)-2-dioxo-5-phenyl-3-oxazolidinebutanoic acid, 1,1-dimethylethyl ester.

Instead of an anti-inflammatory/anti-pain agent, the first component of the combination of the present invention with the hydrogen-generating compound can alternatively be any drug that produces inflammation as an unwanted side effect. The hydrogen-generating compound reduces the amount of inflammation caused by the drug and eliminates the unwanted side effects. It should be understood that anywhere that anti-inflammatory/anti-pain agent is used, the drug that produces inflammation as an unwanted side effect can be used instead where appropriate. Statins (HMG-CoA reductase inhibitors) are one type of drug that produces an unwanted side effect of inflammation (such as myositis, myalgia, and rhabdomyolysis). Statins are generally indicated for lowering cholesterol levels in blood and for preventing heart attacks and stroke. Different statins include atorvastatin, fluvastain, lovastatin, pitavastatin, pravastatin, rosuvastatin, simvastatin, and statin combinations with other agents.

One particular statin that can be used with the hydrogen-generating compound is atorvastatin (LIPITOR®, Pfizer). Atorvastatin is also known as (3R,5R)-7-[2-(4-fluorophenyl)-3-phenyl-4-(phenylcarbamoyl)-5-propan-2-ylpyrrol-1-yl]-3,5-dihydroxyheptanoate, and is described in U.S. Pat. Nos. 4,681,893; 5,273,995; 5,686,104; 6,126,971; and 5,969,156. Atorvastatin calcium is shown below in Formula V:

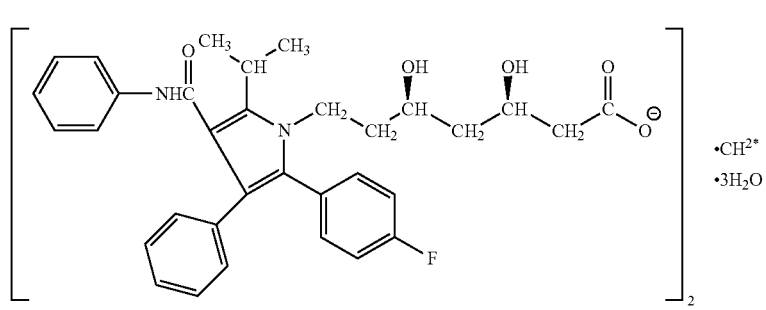

Formula V

Instead of reducing azide (108) to amino acid (109) which requires the addition of acid that causes lactamization of amino acid (109), azide (108) is first hydrolyzed to intermediate azide (108a). Intermediate azide (108a) may be reduced under neutral conditions to give amino acid (109), thus minimizing the problem of lactam formation.

It should also be mentioned that several novel intermediates are produced by the processes discussed herein. Some of these intermediates which are depicted in Charts I, Ia, and II include in the racemate or R or S enantiomer form:

Atorvastatin can be administered in oral form in doses of 10 to 80 mg/day; however, due to synergism with the hydrogen-generating compound, a lower dose can be preferred and normal side effects experienced can be reduced or eliminated. Any other administration methods as described herein can also be used.

The second component of the combination of the present invention is the hydrogen-generating compound. This compound can act to generate an increase of hydrogen in the body by several different methods, such as, but not limited to, releasing hydrogen in the body, or inducing production of hydrogen in the body. The generation of hydrogen can occur anywhere in the body as desired, and can be tailored to occur in a specific site. The hydrogen-generating compound can be H2 itself, or a composition that includes a releasable H2 moiety. Alternatively, the hydrogen-generating compound can be a compound that induces hydrogen to be released by the body itself or by another compound in the body. For example, the hydrogen-generating compound can be any compound that induces bacteria in the stomach to release H2. The hydrogen-generating compound can also be H2 infused liquid that can be a drink or administered by intravenous infusion, or any other method described herein. Combinations of any of the methods of generating hydrogen in the body can also be used.

The hydrogen-generating compound can be a sugar that induces hydrogen production in the stomach. Most preferably, the hydrogen-generating compound is lactulose. The hydrogen-generating compound can also be homologues of lactulose, or other sugars and their homologues. Lactulose is a synthetic sugar that is a disaccharide of a molecule of fructose and a molecule of galactose. It is currently indicated for constipation treatment or for hepatic encephalopathy in removing ammonia from blood. Lactulose is non-absorbable and fermented by intestinal bacteria, resulting in the production of hydrogen. A lactulose hydrogen breath test has previously been used to detect irritable bowel syndrome by detecting an abnormal amount of hydrogen in the breath. However, the creation of hydrogen in the present invention is a positive effect of the compound so that inflammation can be treated. Lactulose can be administered in doses from 40 mL to over 1000 mL per day; however, due to the synergism with the anti-inflammatory/anti-pain agent, a lower dose can be preferred.

Alternatively, the hydrogen-generating compound can be any other monosaccharide, polysaccharide, or other non-saccharide sweetener, such as, but not limited to, glucose, galactose, fructose, mannitol, inulin, sucralose, aspartame, dextrose, maltodextrin, or combinations thereof. One of the preferred hydrogen-generating compounds is inulin, discussed in Example 2.

The hydrogen-generating compound can be delivered at the same time as the anti-inflammatory/anti-pain agent, or at different times. The hydrogen-generating compound can be contained within its own dosage form, within the dosage form together with the anti-inflammatory/anti-pain agent (i.e. a capsule containing the hydrogen-generating compound and the anti-inflammatory/anti-pain agent), or within the dosage form itself (i.e. a capsule coating that includes the hydrogen-generating compound, with the anti-inflammatory/anti-pain agent within the capsule). The composition of the present invention can be tailored to provide different release profiles as needed or desired for a particular patient, such as, but not limited to, sustained release, prolonged release, or immediate release. The hydrogen-generating compound and the anti-inflammatory/anti-pain agent can each have the same release profiles or different release profiles.

Some of the more preferred combinations of the composition of the present invention include pregabalin and lactulose, ibuprofen and lactulose, acetaminophen and lactulose, rofecoxib and lactulose, and celecoxib and lactulose.

The anti-inflammatory/anti-pain agent and hydrogen-generating compound act in a synergistic manner. Therefore, the anti-inflammatory/anti-pain agent is preferably present in an amount that is lower than the normal effective dose. The hydrogen-generating compound can also be present in an amount that is lower than the normal effective dose. In other words, by combining the anti-inflammatory/anti-pain agent with the hydrogen-generating compound, the effective amount needed can be reduced, which in turn reduces unwanted side effects. Therefore, the anti-inflammatory/anti-pain agent and the hydrogen-generating compound can be present in synergistically effective amounts. This combination also allows for the use of anti-inflammatory/anti-pain agents that have previously been thought to be too toxic. As shown below in Example 1, hydrogen generated by the hydrogen-generating compound lactulose showed an additive effect on pregabalin-mediated suppression of pain associated factors (Substance P and nerve growth factor (NGF)) in mice.

The mechanism of action of the present invention is as follows. The hydrogen that is generated from the hydrogen-generating compound affects the total positive/negative charge of neuron cell surfaces to increase their sensitivity to the anti-inflammatory/anti-pain agent. With pregabalin in particular, the anti-pain effect is derived from its blocking of voltage gated calcium channels expressed on neuron cells. These channels' expression level is dependent on the total charge of the neuron cell surface. Other mechanisms of action can alternatively or additionally be present. For example, the hydrogen-generating compound in combination with the anti-inflammatory/anti-pain agent also reduces excessive levels of NGF and Substance P that are present due to inflammation. The combination also reduces or down-regulates expression of IL-1$\beta$, TNF-$\alpha$, and PGE2, all mediators of inflammation and pain.

The composition of the present invention can be used for treating many different diseases and conditions in which inflammation and/or pain are associated. These diseases and conditions can be, but are not limited to, acne vulgaris, asthma, autoimmune diseases, celiac disease, chronic prostatitis, glomerulonephritis, hypersensitivities, inflammatory bowel diseases, pelvic inflammatory disease, reperfusion injury, rheumatoid arthritis, sarcoidosis, transplant rejection, vasculitis, interstitial cystitis, atherosclerosis, allergies, myopathies, leukocyte defects, cancer, endometriosis, and multiple sclerosis. Any of these diseases can be treated according to the methods detailed below.

The present invention provides for a method of treating inflammation and/or pain, by administering an effective amount of the composition including the anti-inflammatory/anti-pain agent and the hydrogen-generating compound to an individual. The anti-inflammatory/anti-pain agent can be any of those described above, and the hydrogen-generating compound can be any of those described above. Administration can be oral, by injection, topical, or any other administration profile described herein. The anti-inflammatory/anti-pain agent and the hydrogen-generating compound preferably act synergistically to treat inflammation and/or pain. By performing this method, side effects normally experienced by patients who are administered anti-inflammatory/anti-pain agents can be reduced by reducing the dose needed due to be effective. The method can further include the step of increasing neuron cell surfaces sensitivity to the anti-inflammatory/anti-pain agent. When the anti-inflammatory/anti-pain agent is pregabalin, the method can also include the step of blocking voltage gated calcium channels expressed on neuron cells. A medical practitioner can confirm that inflammation has been treated in a patient by measuring an amount of IL-1$\beta$, which is a marker for inflammation, or by detecting other markers known in the art. This method can also be performed using a drug that produces inflammation as an unwanted side effect in combination with the hydrogen-generating compound.

The present invention also provides for a method of treating pain, by administering an effective amount of the composition including the anti-inflammatory/anti-pain agent and the hydrogen-generating compound. The anti-inflammatory/anti-pain agent can be any of those described above, and the hydrogen-generating compound can be any of those described above. Administration can be oral, by injection, topical, or any other administration profile described herein. The anti-inflammatory/anti-pain agent and the hydrogen-generating compound preferably act synergistically to treat pain. By performing this method, side effects normally experienced by patients who are administered anti-inflammatory/anti-pain agents can be reduced by reducing the dose needed due to be effective. The method can further include the step of increasing neuron cell surfaces sensitivity to the anti-inflammatory/anti-pain agent. When the anti-inflammatory/anti-pain agent is pregabalin, the method can also include the step of blocking voltage gated calcium channels expressed on neuron cells. A medical practitioner can confirm that pain has been treated in a patient by measuring an amount of nerve growth factor (NGF) or Substance P, which are markers for pain, or by detecting other markers known in the art. This method can also be performed using a drug that produces inflammation as an unwanted side effect in combination with the hydrogen-generating compound.

The present invention also provides a method of potentiating the effects of an anti-inflammatory/anti-pain agent, by administering a synergistically effective amount of the composition including the anti-inflammatory/anti-pain agent and the hydrogen-generating compound. Most preferably, the anti-inflammatory/anti-pain agent is pregabalin and the hydrogen-generating compound is lactulose. Alternatively, the anti-inflammatory/anti-pain agent can be any of those described above, and the hydrogen-generating compound can be any of those described above. Administration can be oral, by injection, topical, or any other administration profile described herein. Because the anti-inflammatory/anti-pain agent and the hydrogen-generating compound interact synergistically, the response and effect on the patient of the anti-inflammatory/anti-pain agent is greater at a particular dose when combined with the hydrogen-generating compound than the response would be alone. Therefore, by performing this method, side effects normally experienced by patients who are administered anti-inflammatory/anti-pain agents can be reduced by reducing the dose needed due to be effective. This method can also be performed using a drug that produces inflammation as an unwanted side effect in combination with the hydrogen-generating compound.

The hydrogen-generating compound can also be used on its own, without the anti-inflammatory/anti-pain agent to reduce inflammation by increasing the amount of hydrogen in the individual. The hydrogen-generating compound reduces inflammation by reducing excessive levels of NGF and Substance P that are present due to inflammation, and by reducing or down-regulating expression of IL-1β, TNF-α, and PGE2. The hydrogen-generating compound can be any hydrogen-generating compound as described above. The hydrogen-generating compound can be used to reduce inflammation caused by any of the diseases described above.

The compounds of the present invention are administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compound of the present invention can be administered in various ways. It should be noted that it can be administered as the compound and can be administered alone or as an active ingredient in combination with pharmaceutically acceptable carriers, diluents, adjuvants and vehicles. The compounds can be administered orally, subcutaneously or parenterally including intravenous, intraarterial, intramuscular, intraperitoneally, intratonsillar, and intranasal administration as well as intrathecal and infusion techniques. Implants of the compounds are also useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

The doses can be single doses or multiple doses over a period of several days. The treatment generally has a length proportional to the length of the disease process and drug effectiveness and the patient species being treated.

When administering the compound of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

The invention is further described in detail by reference to the following experimental examples. These examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

Example 1

Mice were placed in the following administration groups, and administration occurred daily:
1) Control (no treatment) (n=4)
2) Placebo (PBS, i.p.) inoculation—(i.e. CFA only) (n=4)
3) H2 enriched PBS inoculation (i.e. CFA+H2) (n=4)
4) Lactulose inoculation at 0.5 mL/mouse (i.e. CFA+Lact) (n=4)
5) LYRICA® (i.e. CFA+Lyr) (n=5)
6) LYRICA®+H2 enriched PBS (i.e. CFA+Lyr+H2) (n=5)
7) LYRICA®+Lactulose in PBS (i.e. CFA+Lact+H2) (n=4)

CFA was injected into the mice in groups 2 through 7 above. Inflammation was induced in the mice by injection of Freund's complete adjuvant (FCA), 25 µL/foot, on day 0 as shown in FIG. 1A. Chronic inflammation occurred until day 8 (FIG. 1B), when measurements were taken. These measurements included thickness of foot pad (level of inflammation), amount of H2 in abdominal cavity, amount of nerve growth factor (NGF) (pain marker) in foot pad, amount of Substance P (pain marker) in foot pad, and amount of IL-1β in foot pad (level of inflammation).

Figure 2:
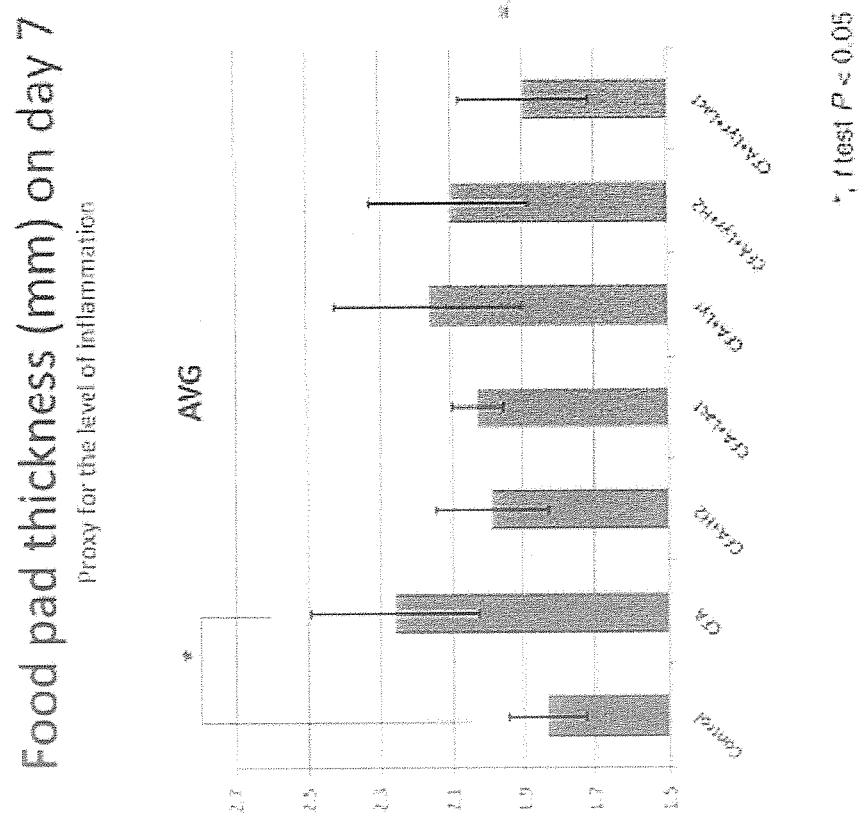
FIG. 2 is a graph of foot pad thickness on day 7.

FIG. 2 shows the results of the foot pad thickness in mm on day 7. Mice in group 2 (receiving only CFA) had the largest foot pad thickness. Mice in group 7 receiving LYRICA® plus lactulose had the smallest foot pad thickness (besides control). While mice in group 6 (CFA+Lyr+H2) had smaller foot pad thickness than mice in group 5 (CFA+Lyr), mice in group 7 had a significantly lower foot pad thickness than mice in group 5. Thus, LYRICA® and lactulose acted synergistically in reducing foot pad thickness.

Figure 3:
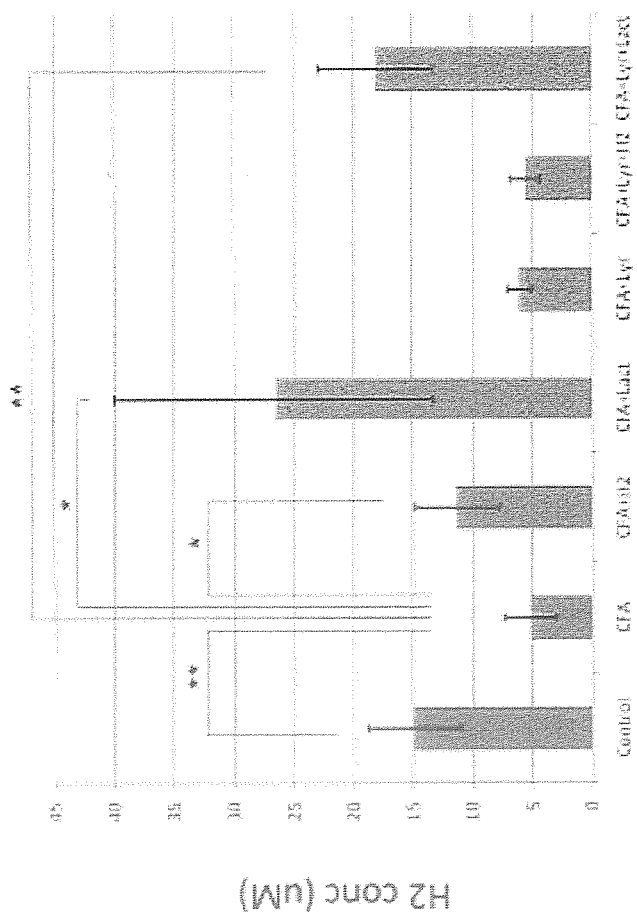
FIG. 3 is a graph of H2 concentration in the abdomen on day 8.

FIG. 3 shows the measurement of H2 concentration in the abdomen of the mice on day 8. H2 concentration was highest with group 4, and still high with group 7. This confirms that lactulose induces the production of hydrogen in the abdomen.

Figure 4:
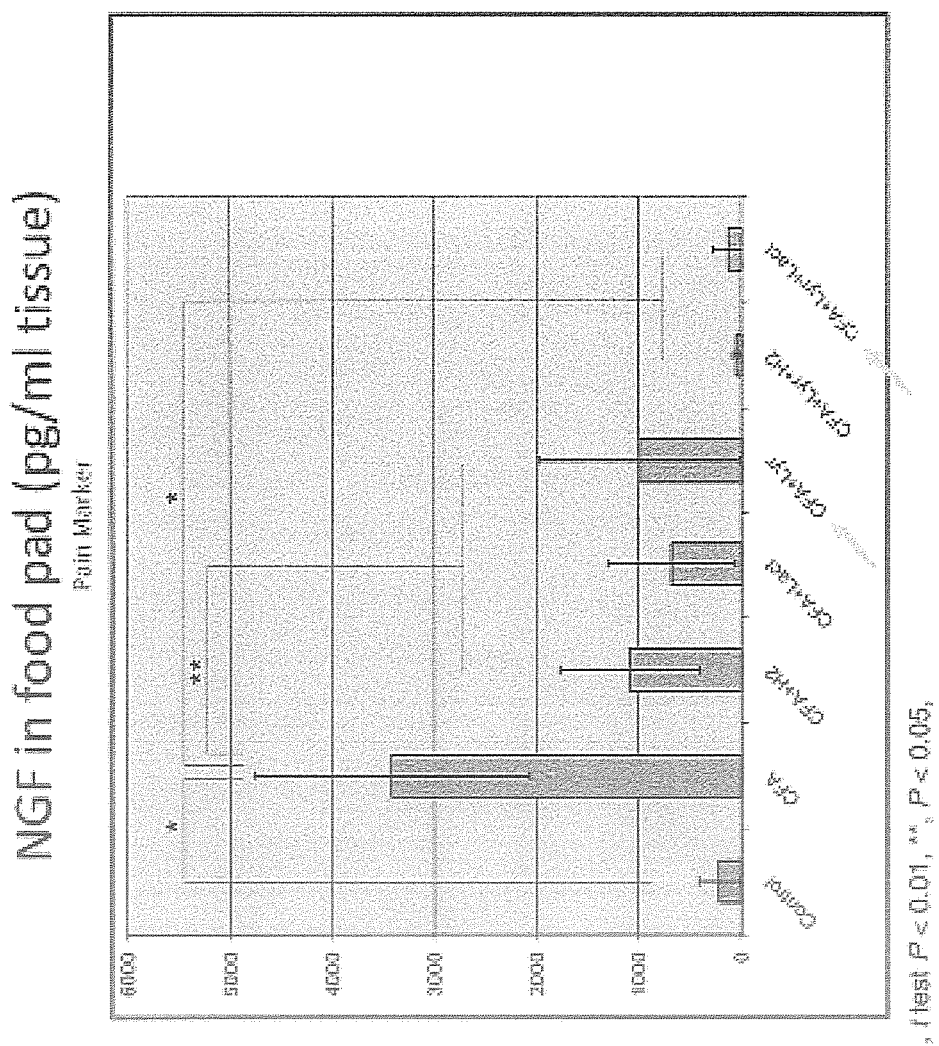
FIG. 4 is a graph of NGF in the foot pad.

FIG. 4 shows the measurement of the pain marker NGF in the foot pad of mice. Large amounts of NGF were found in the mice of group 2 (CFA only). Both groups 6 and 7 of the mice showed very reduced amounts of NGF. This confirms that LYRICA® and a hydrogen-generating compound (either H2 enriched PBS or lactulose) can reduce pain.

Figure 5:
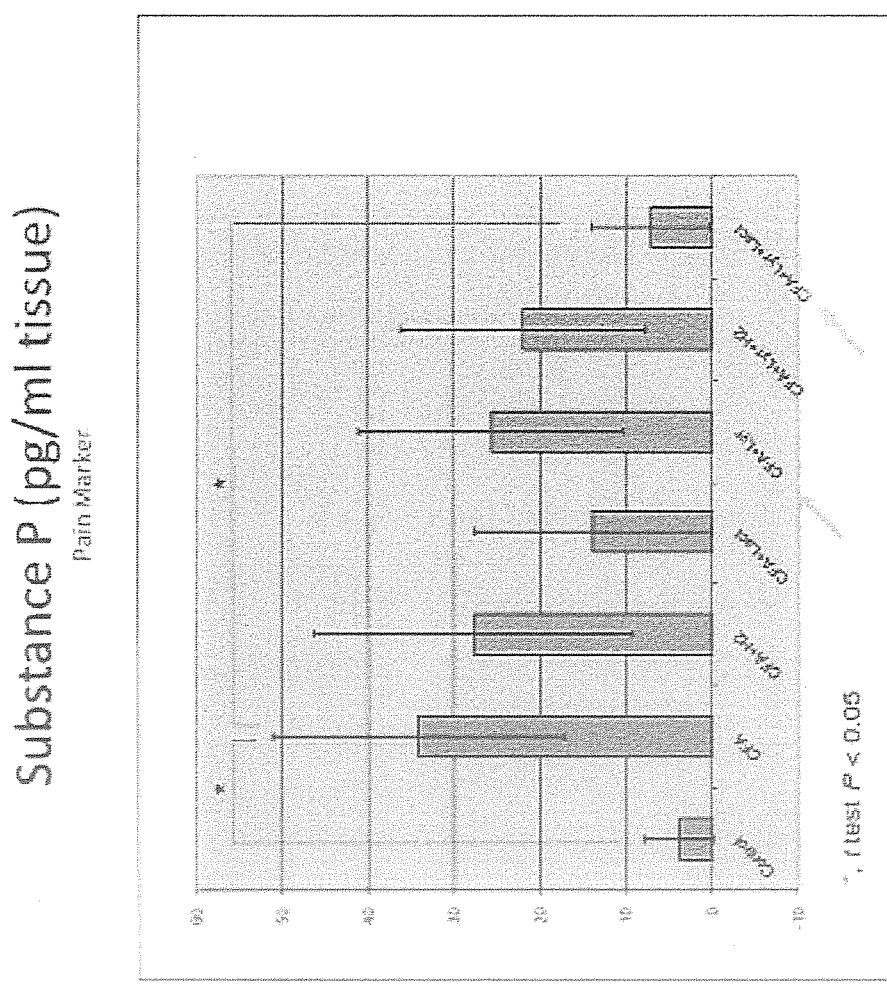
FIG. 5 is a graph of substance P (pain marker)

FIG. 5 shows the measurement of the pain marker Substance P in the tissue of mice. Mice in group 5 showed a reduction in the marker compared to the placebo group 2. Mice in group 6 showed lower levels of the marker than group 5; however, mice in group 7 showed a significantly lower level of the marker than the mice in group 5. This confirms that LYRICA® and lactulose acted synergistically in reducing the pain marker Substance P, and thus acted synergistically in reducing pain.

Figure 6:
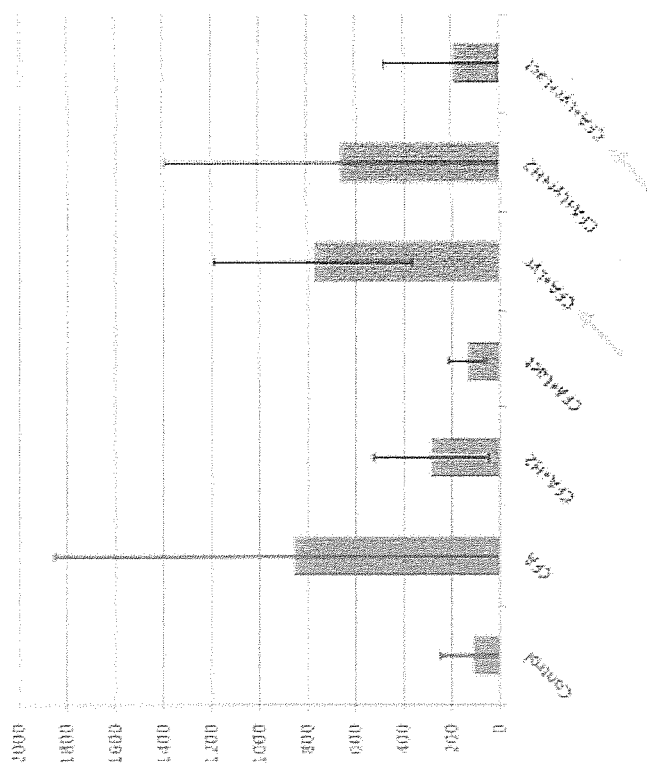
FIG. 6 is a graph of levels of IL-1β in tissue.

FIG. 6 shows the measurement of IL-1β in tissue of the mice as an indication of the level of inflammation. Mice in group 5 had slightly reduced levels of inflammation compared to placebo group 2. Mice in group 6 showed lower levels of inflammation than group 5; however, mice in group 7 showed significantly lower levels of inflammation than the mice in group 5. This confirms that LYRICA® and lactulose acted synergistically in reducing levels of IL-1β, and thus acted synergistically in reducing inflammation.

Example 2

Inulin is increasingly used in processed foods because it has unusually adaptable characteristics. Inulin is a starchy substance found in a wide variety of fruits, vegetables, and herbs, including wheat, garlic, onions, bananas, leeks, artichokes, and asparagus. The inulin that is used for medicine is most commonly obtained by soaking chicory roots in hot water.

Its flavor ranges from bland to subtly sweet (approx. 10% sweetness of sugar/sucrose). It can be used to replace sugar, fat, and flour. This is advantageous because inulin contains 25-35% of the food energy of carbohydrates (starch, sugar). While inulin is a versatile ingredient, it also has health benefits. Inulin increases calcium absorption and possibly magnesium absorption. It supports the growth of a special kind of bacteria that are associated with improving bowel function and general health. Inulin also decreases the body's ability to make certain kinds of fats. In terms of nutrition, it is considered a form of soluble fiber and is sometimes categorized as a prebiotic. Due to the body's limited ability to process fructans, inulin has minimal increasing impact on blood sugar, and—unlike fructose—is not insulemic and does not raise triglycerides.

Figure 7:
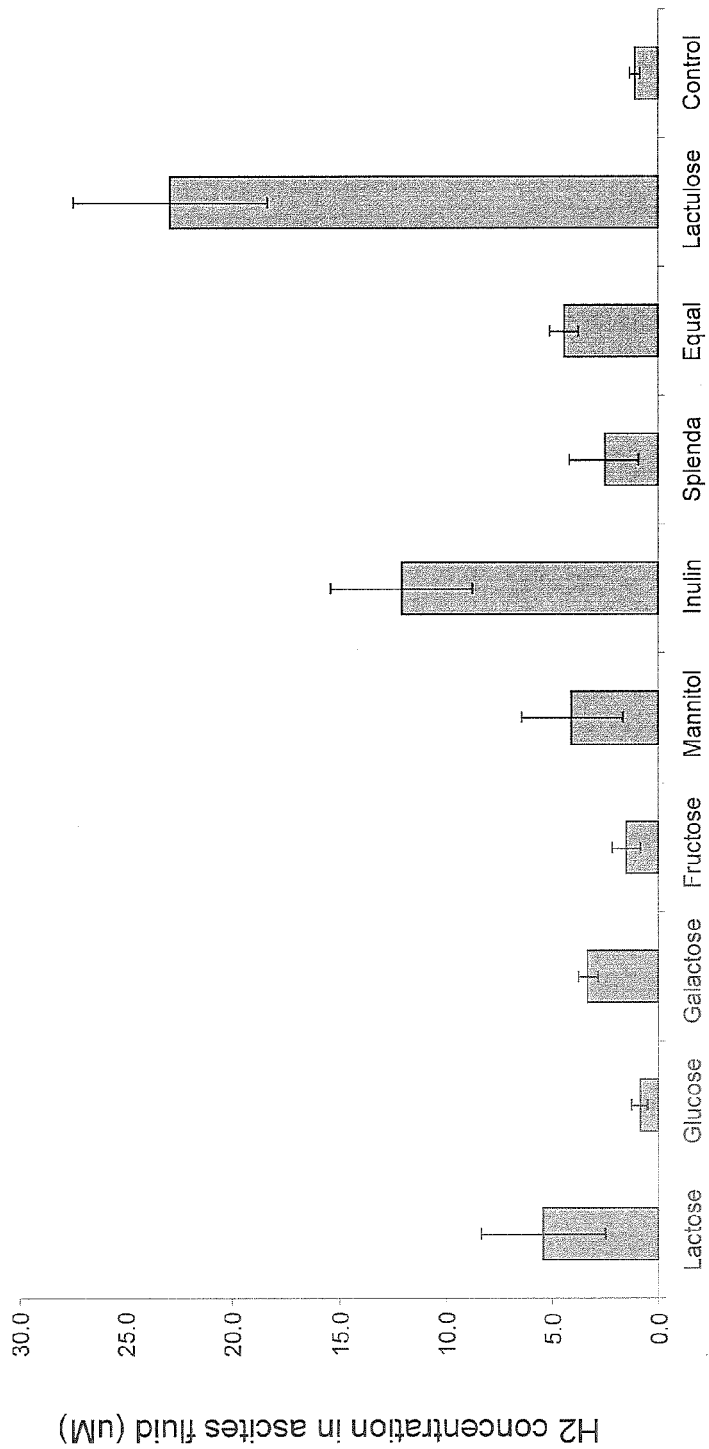
FIG. 7 is a graph of H2 concentration in ascites fluid after ingestion of sugar solution.

FIG. 7 shows the increased H2 in mouse abdominal cavities after ingestion of various sugar solutions. Lactose, glucose, galactose, fructose, mannitol, inulin, Splenda® (McNeil Nutritionals (sucralose)), Equal® (Merisant (aspartame, dextrose, and maltodextrin)), and lactulose were tested along with a control. Lactulose provided the highest concentration of H2 in ascites fluid and inulin provided the next highest concentration.

Figure 8:
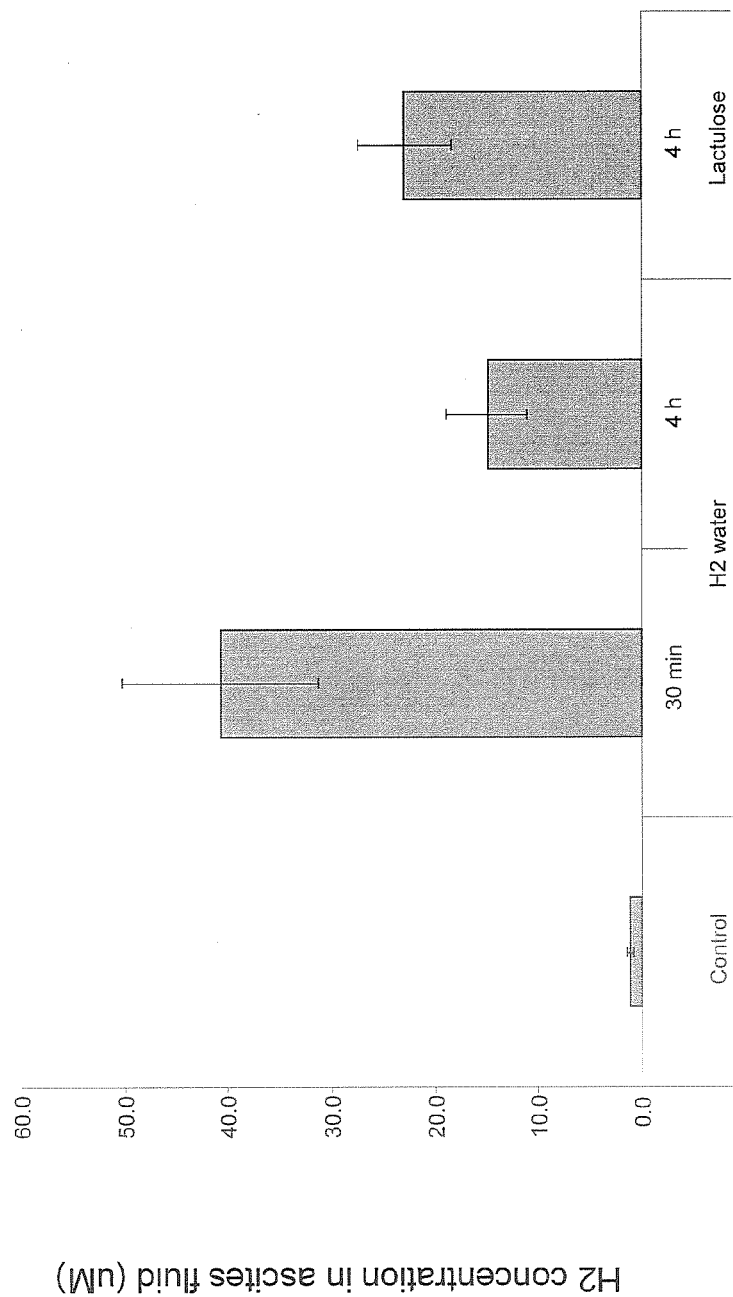
FIG. 8 is a graph of H2 concentration in ascites fluid after ingestion of H2-enriched water versus lactulose.

FIG. 8 shows a comparison of H2-enriched water versus lactulose on the concentration of H2 in ascites fluid. After 30 minutes, H2-enriched water provided approximately 40 µM H2 concentration but dropped off to approximately 15 µM after 4 hours. At 4 hours, lactulose provided over 20 µM H2 concentration.

Figure 9B:
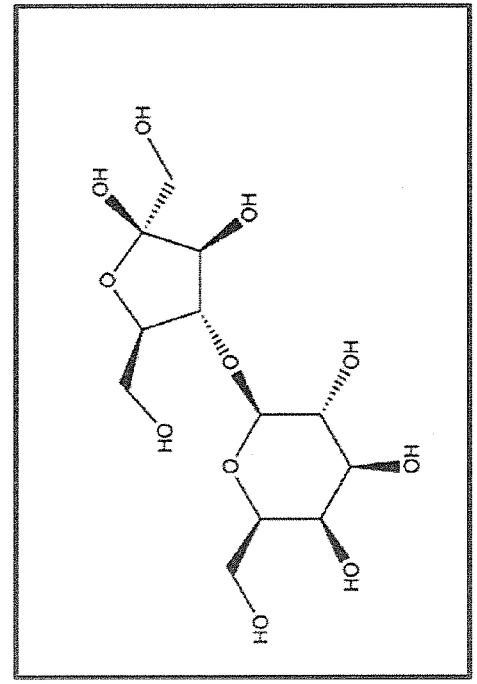
FIG. 9A is a depiction of inulin and FIG. 9B is a depiction of lactulose.
Figure 9A:
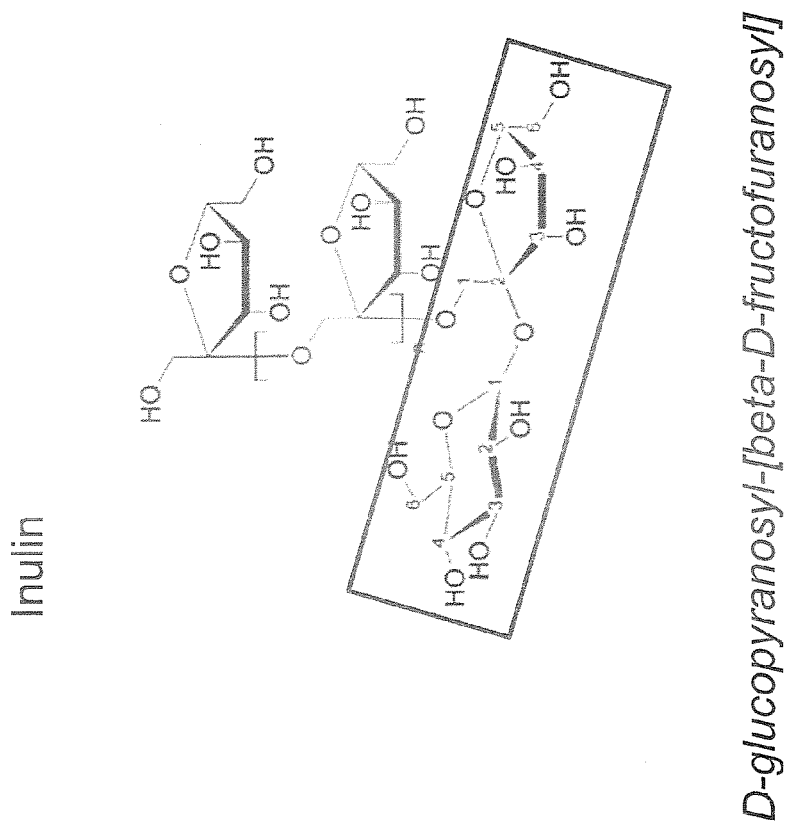

FIGS. 9A and 9B show the chemical structure of inulin and lactulose. Similar structure of the two compounds is boxed.

Example 3

Figure 10:
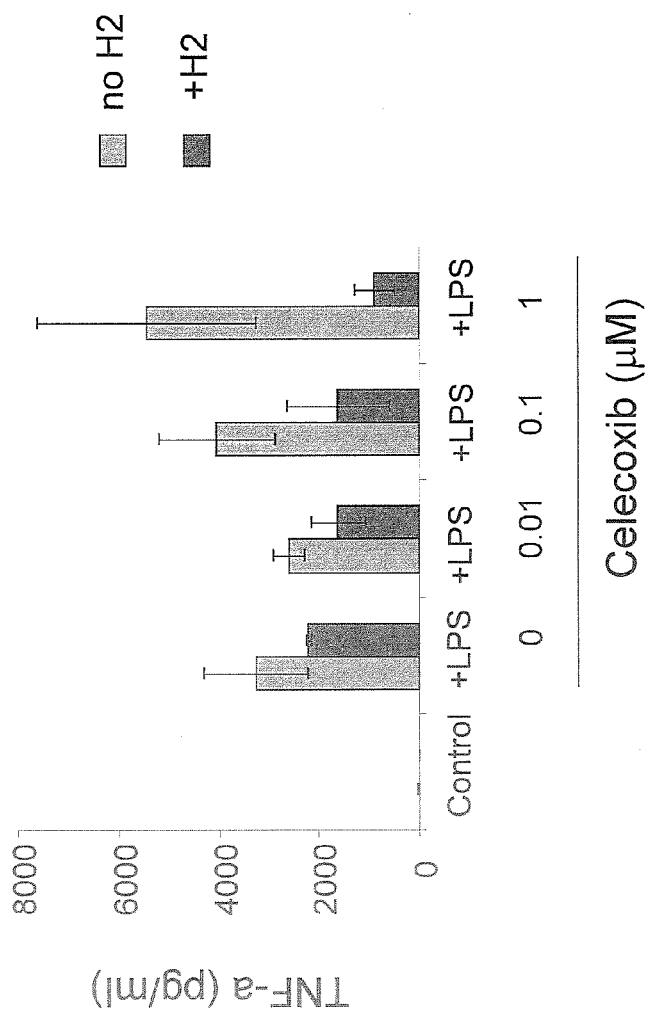
FIG. 10 is a graph of H2 attenuated Celecoxib-mediated promotion of TNF-α production from LPS-stimulated mouse macrophages.
Figure 11:
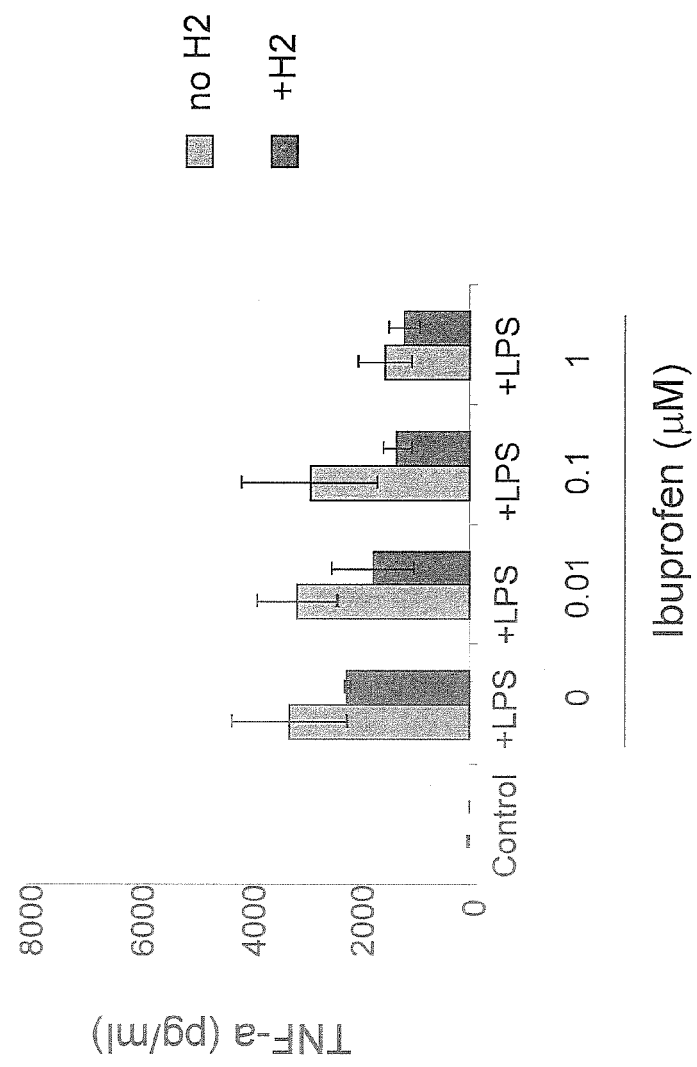
FIG. 11 is a graph of the effects of H2 on ibuprofen-mediated TNF-α suppression.

The following is an in vitro experiment to test the effects of hydrogen on the Celecoxib- or Ibuprofen-mediated anti-inflammatory activities, and the results are shown in FIGS. 10 and 11.

The mouse macrophage cell line (RAW264.7) was seeded at a density of 1.0×10⁵ cells/well in 96-well culture plates in Minimum Essential Medium Alpha (−MEM, Sigma) supplemented with penicillin G solution (100 U/ml, GIBCO; Invitrogen, Buffalo, N.Y.), streptomycin (100 g/ml, GIBCO; Invitrogen), and gentamicin (50 g/ml, GIBCO; Invitrogen) containing 10% FBS in the presence or absence of $H_2$ (300 nM/ml) for 30 min. Then the cells were exposed to LPS (0.1 mg/ml, Invivogen, San Diego, Calif.), with or without a variety of concentrations of Celecoxib or Ibuprofen (10-1000 nM). After culture of the RAW264.7 cells for 24 hours in a $CO_2$ incubator (37° C.), the culture supernatant was harvested and subjected to TNF-α ELISA (R&D Systems).

As shown in FIG. 10, H2 in combination with Celecoxib greatly reduced the amount of TNF-α production in the macrophages as compared to Celecoxib administered alone, especially at the 1 µM dose. Also, as shown in FIG. 11, H2 in combination with Ibuprofen reduced TNF-α production in the macrophages as compared to Ibuprofen administered alone, especially at the 0.1 dose. Therefore, H2 administered with either Celecoxib or Ibuprofen is capable of reducing inflammation in a greater amount than the Celecoxib or Ibuprofen alone.

Example 4

The following experiment was performed to test the effects of Lactulose combined with Celecoxib or Ibuprofen on Freund's complete adjuvant-induced hind paw inflammation in mice, with the results shown in FIGS. 12-15.

For induction of hindpaw inflammation, mice (BALB/c; 8 w old male n=6/group) received i.pl. injection of 25 µl of complete Freund's adjuvant (CFA, diluted 1:1 with PBS, 2 mg/ml; *Mycobacterium tuberculosis*; Difco Laboratories, Detroit, Mich.). Lactulose (10% water) or control water alone was administered once in a day for 7 days (500 µl/day) by oral gavage using a 20-G bulb-tipped gastric gavage needle (P.O.). Celecoxib (Toronto Research Chemicals) and Ibuprofen (Enzo Life Sciences) dissolved in PBS was applied to mice once a day via intra-peritoneal (i.p.) injection (10 mg/kg/day, respectively) for 7 days. The thickness of the foot pad was measured using a digital microcaliper as mice were sacrificed on 7 day. Surgically removed hind paw tissue was homogenized in EIA-Buffer (Cayman) and subjected to mouse NGF ELISA (Millipore), PGE2 EIA (Cayman), or TNF-α ELISA (R&D systems).

Figure 12:
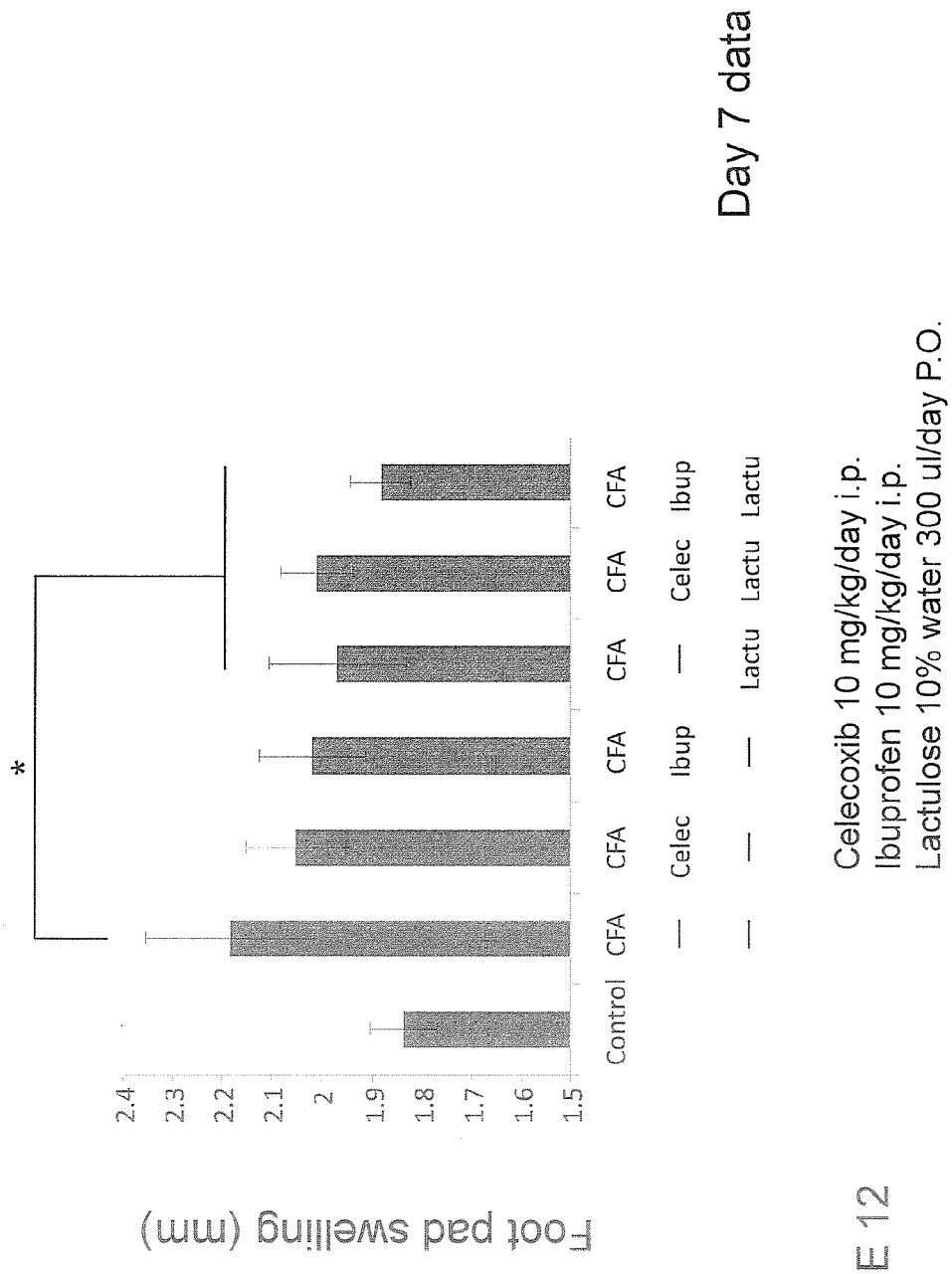
FIG. 12 is a graph of mouse FCA induced foot pad inflammation.
Figure 13:
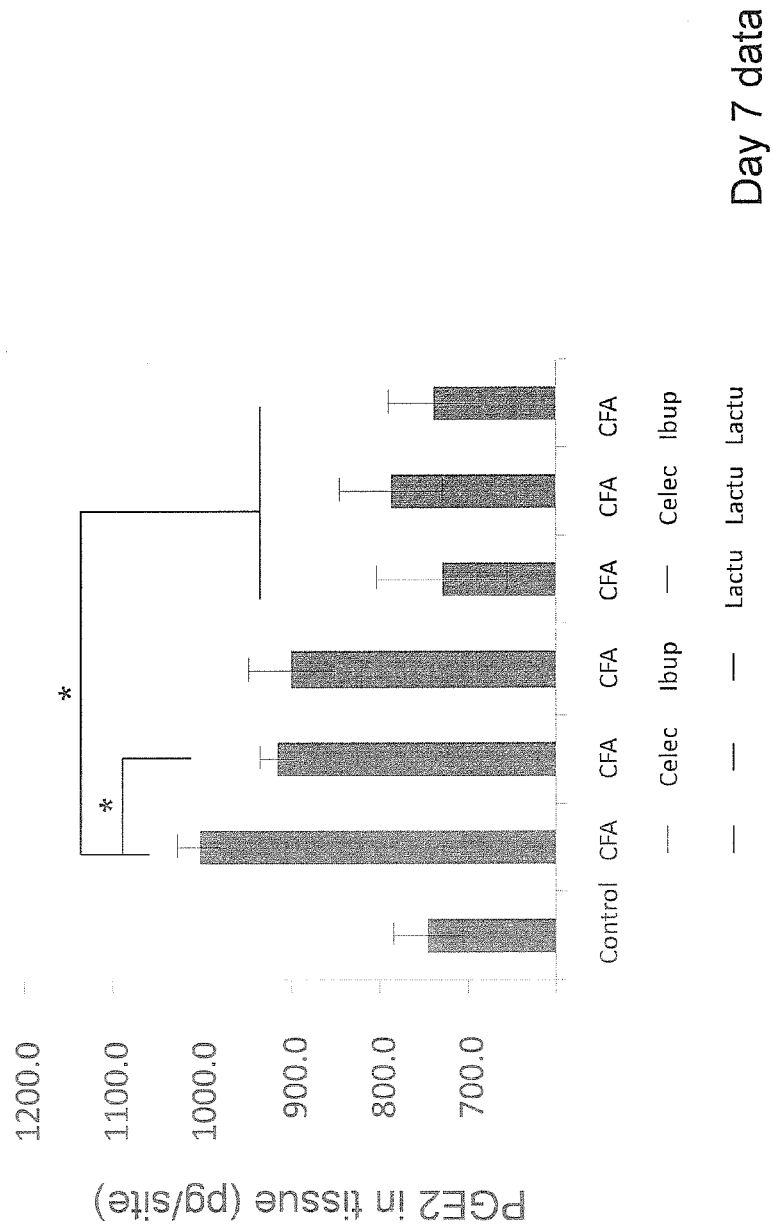
FIG. 13 is a graph of the measurement of PGE2 in inflamed foot pads.
Figure 14:
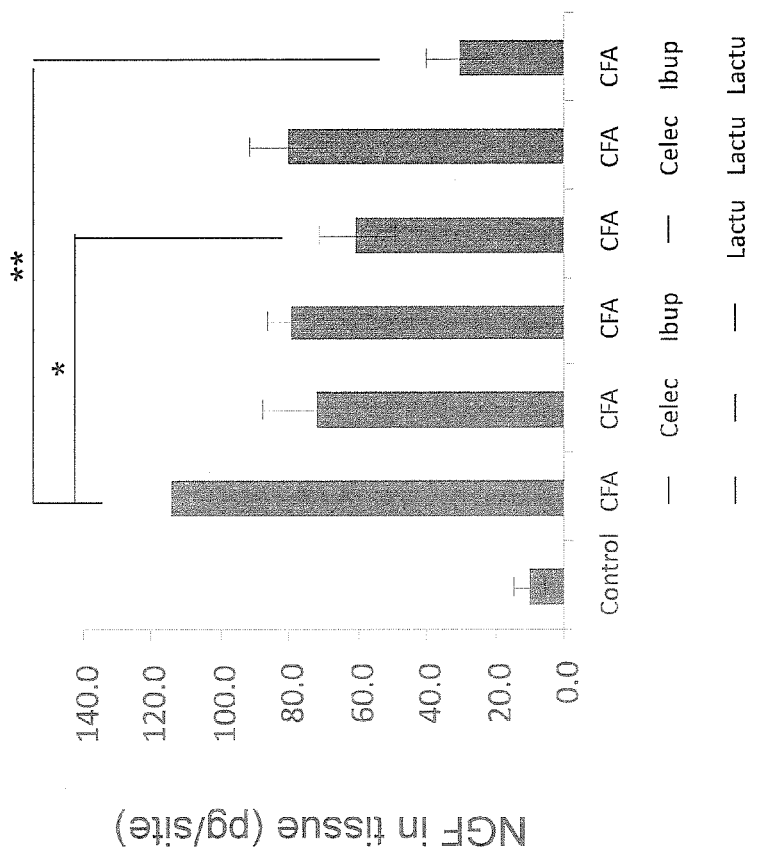
FIG. 14 is a graph of the measurement of NGF in inflamed foot pads.
Figure 15:
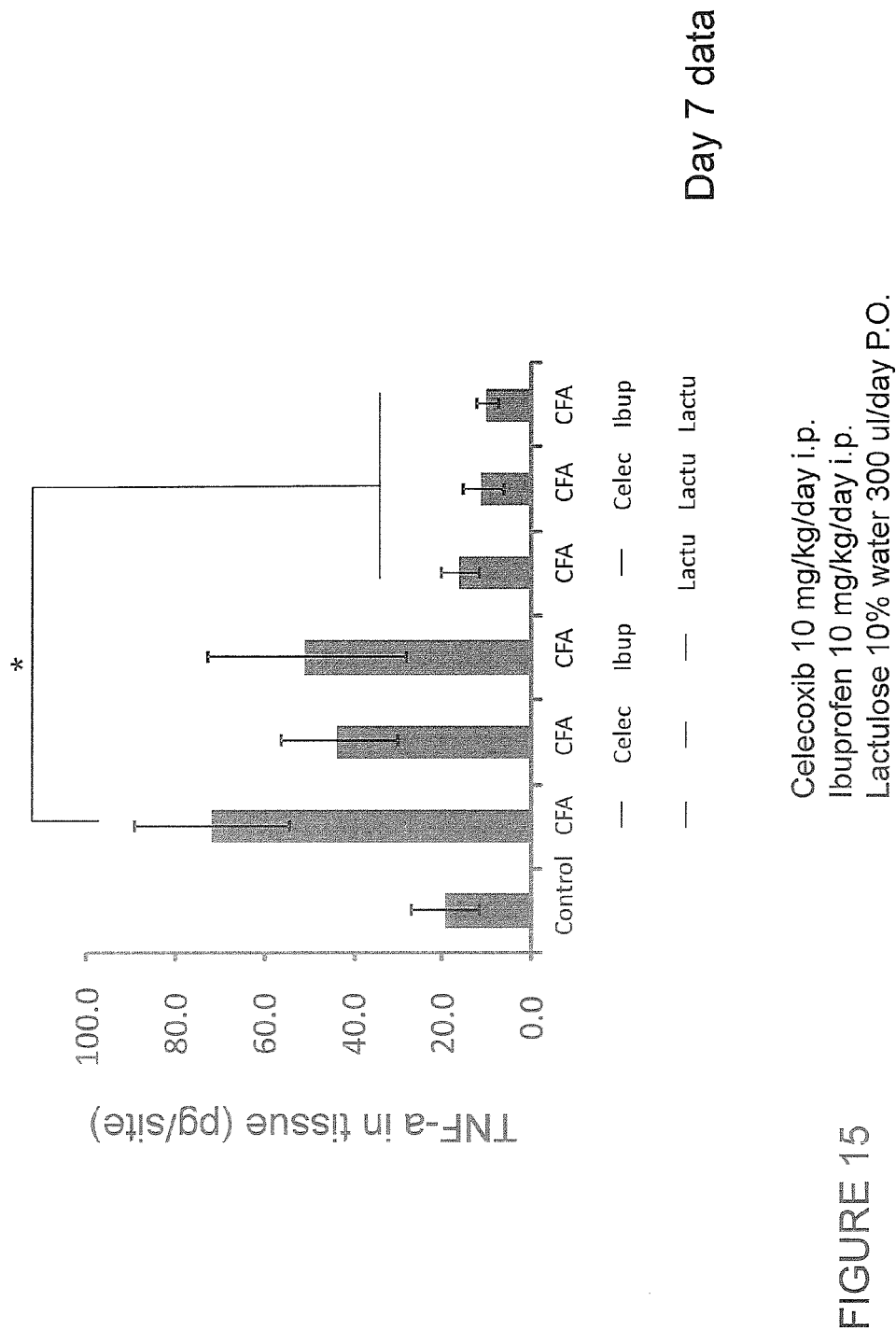
FIG. 15 is a graph of the measurement of TNF-α in inflamed foot pads.

As shown in FIG. 12, foot pad swelling was reduced in mice given CFA+lactulose, CFA+Celecoxib+lactulose, and CFA+Ibuprofen+lactulose, as compared to mice who did not receive lactulose. FIG. 13 shows that the amount of PGE2 was reduced in mice given CFA+lactulose, CFA+Celecoxib+lactulose, and CFA+Ibuprofen+lactulose, as compared to mice who did not receive lactulose. FIG. 14 shows that NGF was reduced in mice given CFA+lactulose, and CFA+Ibuprofen+lactulose, as compared to mice who did not receive lactulose. FIG. 15 shows that the amount of TNF-α was greatly reduced in mice given CFA+lactulose, CFA+Celecoxib+lactulose, and CFA+Ibuprofen+lactulose, as compared to mice who did not receive lactulose. Therefore, lactulose plus either Celecoxib or Ibuprofen is capable of reducing inflammation in a greater amount than the Celecoxib or Ibuprofen alone.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A composition for treating inflammation and pain, comprising synergistic amounts of an anti-inflammatory agent or anti-pain agent in combination with a hydrogen-generating compound of lactulose in an amount lower than indicated for treating constipation, said amount being less than 10 g/day.

2. The composition of claim 1, wherein said anti-inflammatory or anti-pain agent is chosen from the group consisting of non-steroidal anti-inflammatory drugs (NSAIDS), steroids, immune selective anti-inflammatory derivatives (ImSAIDs), narcotics, analgesics, biologic agents, and combinations thereof.

3. The composition of claim 2, wherein said NSAID is ibuprofen.

4. The composition of claim 3, wherein said ibuprofen is in an amount of 200 to 300 mg per day.

5. The composition of claim 2, wherein said NSAID is celecoxib.

6. The composition of claim 5, wherein said celecoxib is in an amount of 50 to 400 mg per day.

7. The composition of claim 2, wherein said NSAID is rofecoxib.

8. The composition of claim 7, wherein said rofecoxib is in an amount of 12.5 to 50 mg per day.

9. The composition of claim 1, wherein said anti-inflammatory or anti-pain agent is pregabalin.

10. The composition of claim 9, wherein said pregabalin is in an amount of 25 to 600 mg per day.

11. The composition of claim 9, wherein said pregabalin is chosen from the group consisting of the S-enantiomer of 3-(aminomethyl)-5-methyl-hexanoic acid, (S)-(+)-enantiomer of 4-amino-3-(2-methylpropyl)butanoic acid, and the (R)(−)-enantiomer of 4-amino-3-(2-methylpropyl)butanoic acid.

12. The composition of claim 1, wherein said hydrogen-generating compound is chosen from the group consisting of H2 molecules, a prodrug releasing H2, a compound that causes the release of H2 within the body, and combinations thereof.

13. The composition of claim 1, wherein said hydrogen-generating compound is a compound that induces bacteria in the stomach to release H2.

14. The composition of claim 1, wherein said hydrogen-generating compound is an H2 infused liquid.

15. The composition of claim 1, wherein said hydrogen-generating compound is a sugar that induces hydrogen production in the stomach chosen from the group consisting of lactulose, glucose, galactose, fructose, mannitol, inulin, sucralose, aspartame, dextrose, maltodextrin, and combinations thereof.

16. The composition of claim 1, wherein said composition is in a dosage form is chosen from the group consisting of the hydrogen-generating compound in its own dosage form different from a dosage form of the anti-inflammatory or anti-pain agent, the hydrogen-generating compound and the anti-inflammatory or anti-pain agent in the same dosage form, or the hydrogen-generating compound within a coating of the dosage form and the anti-inflammatory or anti-pain agent within the dosage form.

17. The composition of claim 1, wherein said composition is chosen from the group consisting of pregabalin and lactulose, ibuprofen and lactulose, acetaminophen and lactulose, rofecoxib and lactulose, and celecoxib and lactulose.

18. A composition for treating inflammation and pain, comprising synergistically effective amounts of pregabalin and lactulose in an amount of lower than indicated for treating constipation, said amount being less than 10 g/day.

* * * * *